US 7,536,228 B2

(12) United States Patent
Shaolian et al.

(10) Patent No.: US 7,536,228 B2
(45) Date of Patent: May 19, 2009

(54) ACTIVATION DEVICE FOR DYNAMIC RING MANIPULATION

(75) Inventors: Samuel Shaolian, Newport Beach, CA (US); Shahram Moaddeb, Irvine, CA (US); Maurice Buchbinder, La Jolla, CA (US); David Zarbatany, Laguna Niguel, CA (US); Jason Tran, Santa Ana, CA (US)

(73) Assignee: MiCardia Corporation, Irvine, CA (US)

( * ) Notice: Subject to any disclaimer, the term of this patent is extended or adjusted under 35 U.S.C. 154(b) by 0 days.

(21) Appl. No.: 11/728,010

(22) Filed: Mar. 22, 2007

(65) Prior Publication Data

US 2007/0239154 A1    Oct. 11, 2007

Related U.S. Application Data

(60) Provisional application No. 60/785,912, filed on Mar. 24, 2006.

(51) Int. Cl.
*A61N 1/18* (2006.01)
(52) U.S. Cl. ...................................... 607/119
(58) Field of Classification Search ................ 607/116, 607/119, 122, 128
See application file for complete search history.

(56) References Cited

U.S. PATENT DOCUMENTS

| | | | |
|---|---|---|---|
| 3,868,956 A | 3/1975 | Alfidi et al. | |
| 4,233,690 A | 11/1980 | Akins | |

(Continued)

FOREIGN PATENT DOCUMENTS

CA    2132730    6/1994

(Continued)

OTHER PUBLICATIONS

Lendlein et al.; Biodegradable, Elastic Shape Memory Polymers for Potential Biomedical Applications; Sciencexpress; Apr. 25, 2002; pp. 1-10.

(Continued)

*Primary Examiner*—George R Evanisko
*Assistant Examiner*—Joseph M Dietrich
(74) *Attorney, Agent, or Firm*—Knobbe, Martens, Olson & Bear, LLP

(57) ABSTRACT

An activation device for applying energy to an implanted annuloplasty ring is described. In some embodiments, the activation device includes an outer elongate member having an outer elongate member distal end and an outer elongate member proximal end, and a lumen therebetween. In some embodiments, the activation device further includes an inner elongate member having a inner elongate member distal end and a inner elongate member proximal end, and a lumen therebetween, wherein the inner elongate member is slidably insertable through the lumen of the outer elongate member. In some embodiments, the activation device further includes at least one adjustable spline having spline proximal and spline distal ends, the spline distal end connected to the inner tubular member distal end and the spline proximal end connected to the outer tubular member distal end, wherein the adjustable spline is configured to flex as the inner tubular member distal end is drawn proximally toward the outer tubular member distal end while the inner elongate member resides in the lumen of the outer elongate member. In some embodiments, the activation device further includes at least one energy-transfer element coupled to the adjustable spline.

11 Claims, 15 Drawing Sheets

U.S. PATENT DOCUMENTS

| | | | |
|---|---|---|---|
| 4,507,115 A | | 3/1985 | Kambara |
| 4,574,782 A | | 3/1986 | Borrelli et al. |
| 4,633,875 A | | 1/1987 | Turner |
| 4,660,571 A | * | 4/1987 | Hess et al. ............ 607/116 |
| 4,665,906 A | | 5/1987 | Jervis |
| 4,805,618 A | | 2/1989 | Ueda et al. |
| 4,940,064 A | * | 7/1990 | Desai ............ 607/122 |
| 5,010,897 A | | 4/1991 | Leveen |
| 5,099,576 A | | 3/1992 | Shinmura |
| 5,122,136 A | | 6/1992 | Guglielmi et al. |
| 5,171,252 A | | 12/1992 | Friedland |
| 5,217,484 A | | 6/1993 | Marks |
| 5,255,679 A | * | 10/1993 | Imran ............ 607/122 |
| 5,290,300 A | | 3/1994 | Cosgrove |
| 5,350,413 A | | 9/1994 | Miller |
| 5,401,241 A | | 3/1995 | Delany |
| 5,415,623 A | | 5/1995 | Cherubini |
| 5,509,888 A | | 4/1996 | Miller |
| 5,850,837 A | | 12/1998 | Shiroyama et al. |
| 5,882,302 A | | 3/1999 | Driscoll, Jr. et al. |
| 5,979,456 A | | 11/1999 | Magovern |
| 6,093,883 A | | 7/2000 | Sanghvi et al. |
| 6,160,084 A | | 12/2000 | Langer et al. |
| 6,167,313 A | | 12/2000 | Gray et al. |
| 6,273,908 B1 | | 8/2001 | Ndondo-Lay |
| 6,306,133 B1 | * | 10/2001 | Tu et al. ............ 606/41 |
| 6,388,043 B1 | | 5/2002 | Langer et al. |
| 6,397,109 B1 | | 5/2002 | Cammilli et al. |
| 6,406,493 B1 | | 6/2002 | Tu et al. |
| 6,425,867 B1 | | 7/2002 | Vaezy et al. |
| 6,599,234 B1 | | 7/2003 | Gray et al. |
| 6,718,985 B2 | | 4/2004 | Hlavka et al. |
| 6,720,402 B2 | | 4/2004 | Langer et al. |
| 6,740,094 B2 | | 5/2004 | Maitland et al. |
| 6,786,904 B2 | | 9/2004 | Doscher et al. |
| 6,805,711 B2 | | 10/2004 | Quijano et al. |
| 6,889,093 B1 | * | 5/2005 | Flammang ............ 607/122 |
| 7,101,395 B2 | | 9/2006 | Tremulis et al. |
| 7,285,087 B2 | | 10/2007 | Moaddeb et al. |
| 7,297,150 B2 | | 11/2007 | Cartledge et al. |
| 2002/0133223 A1 | | 9/2002 | Vito et al. |
| 2002/0133225 A1 | | 9/2002 | Gordon |
| 2003/0055198 A1 | | 3/2003 | Langer et al. |
| 2003/0135267 A1 | | 7/2003 | Solem et al. |
| 2003/0139787 A1 | | 7/2003 | Eggers et al. |
| 2003/0191528 A1 | | 10/2003 | Quijano et al. |
| 2003/0216657 A1 | * | 11/2003 | Holmstrom et al. ......... 600/509 |
| 2004/0087899 A1 | | 5/2004 | Weber et al. |
| 2004/0249453 A1 | | 12/2004 | Cartledge et al. |
| 2004/0250820 A1 | | 12/2004 | Forsell |
| 2005/0033446 A1 | * | 2/2005 | Deem et al. ............ 623/23.6 |
| 2005/0119733 A1 | | 6/2005 | Williams et al. |
| 2005/0288776 A1 | | 12/2005 | Shaoulian et al. |
| 2007/0299543 A1 | | 12/2007 | Cartledge et al. |

FOREIGN PATENT DOCUMENTS

| | | |
|---|---|---|
| WO | WO 94/12101 | 6/1994 |
| WO | WO 96/34211 | 10/1996 |
| WO | WO 2004/019826 | 3/2004 |
| WO | WO 2007/033360 | 3/2007 |

OTHER PUBLICATIONS

Ryklina et al.; Two-way Shape Memory Effect Inducing in NiTi Alloy and its Application to a Device for Clipping Blood Vessels; Proceedings of the International Conference on Shape Memory and Superelastic Technologies; Oct. 3-7, 2004; pp. 51; Baden-Baden Germany.

Cribier et al.; Early Experience with Percutaneous Transcatheter Implantation of Heart Valve Prosthesis for the Treatment of End-Stage Inoperable Patients with Calcific Aortic Stenosis; Journal of the American College of Cardiology; 2004; pp. 698-703; vol. 43.

Vaezy et al.; Image-Guided Acoustic Therapy; Annu. Rev. Biomed. Eng.; 2001; pp. 375-390; vol. 3.

* cited by examiner

ACTIVATION DEVICE FOR DYNAMIC RING MANIPULATION

CROSS REFERENCE TO RELATED APPLICATIONS

This application claims the benefit under 35 U.S.C. §119 (e) of U.S. Provisional Patent Application No. 60/785,912, filed on Mar. 24, 2006, and titled ACTIVATION CATHETER FOR DYNAMIC RING MANIPULATION, the entirety of which is hereby incorporated by reference.

BACKGROUND OF THE INVENTION

1. Field of the Invention

The present invention relates to methods and devices for reinforcing dysfunctional heart valves and other body structures. More specifically, the present invention relates to dynamically shaped annuloplasty rings that can be adjusted within the body of a patient and medical devices applying energy to a dynamically shaped annuloplasty ring used to reshape the mitral valve repair 2. Description of the Related Art The circulatory system of mammals includes the heart and the interconnecting vessels throughout the body that include both veins and arteries. The human heart includes four chambers, which are left atrium, the right atrium, the left ventricle, and the right ventricle. The mitral valve, which allows blood flow in one direction, is positioned between the left ventricle and left atrium. The tricuspid valve is positioned between the right ventricle and the right atrium. The aortic valve is positioned between the left ventricle and the aorta, and the pulmonary valve is positioned between the right ventricle and pulmonary artery. The heart valves function in concert to move blood throughout the circulatory system. The right ventricle pumps oxygen-poor blood from the body to the lungs and then into the left atrium. From the left atrium, the blood is pumped into the left ventricle and then out the aortic valve into the aorta. The blood is then recirculated throughout the tissues and organs of the body and returns once again to the right atrium.

If the valves of the heart do not function properly, due either to disease or congenital defects, the circulation of the blood may be compromised. Diseased heart valves may be stenotic, wherein the valve does not open sufficiently to allow adequate forward flow of blood through the valve, and/or incompetent, wherein the valve does not close completely. Incompetent heart valves cause regurgitation or excessive backward flow of blood through the valve when the valve is closed. For example, certain diseases of the heart valves can result in dilation of the heart and one or more heart valves. When a heart valve annulus dilates, the valve leaflet geometry deforms and causes ineffective closure of the valve leaflets. The ineffective closure of the valve can cause regurgitation of the blood, accumulation of blood in the heart, and other problems.

Diseased or damaged heart valves can be treated by valve replacement surgery, in which damaged leaflets are excised and the annulus is sculpted to receive a replacement valve. Another repair technique that has been shown to be effective in treating incompetence is annuloplasty, in which the effective size of the valve annulus is contracted by attaching a prosthetic annuloplasty repair segment or ring to an interior wall of the heart around the valve annulus. The annuloplasty ring reinforces the functional changes that occur during the cardiac cycle to improve coaptation and valve integrity. Thus, annuloplasty rings help reduce reverse flow or regurgitation while permitting good hemodynamics during forward flow.

Generally, annuloplasty rings comprise an inner substrate of a metal such as stainless steel or titanium, or a flexible material such as silicon rubber or Dacron®. The inner substrate is generally covered with a biocompatible fabric or cloth to allow the ring to be sutured to the heart tissue. Annuloplasty rings may be stiff or flexible, may be open or closed, and may have a variety of shapes including circular, D-shaped, or C-shaped. The configuration of the ring is generally based on the shape of the heart valve being repaired or on the particular application. For example, the tricuspid valve is generally circular and the mitral valve is generally D-shaped. Further, C-shaped rings may be used for tricuspid valve repairs, for example, because it allows a surgeon to position the break in the ring adjacent the atrioventricular node, thus avoiding the need for suturing at that location.

Annuloplasty rings support the heart valve annulus and restore the valve geometry and function. Although the implantation of an annuloplasty ring can be effective, the heart of a patient may change geometry over time after implantation. For example, the heart of a child will grow as the child ages. As another example, after implantation of an annuloplasty ring, dilation of the heart caused by accumulation of blood may cease and the heart may begin returning to its normal size. Whether the size of the heart grows or reduces after implantation of an annuloplasty ring, the ring may no longer be the appropriate size for the changed size of the valve annulus.

The standard annuloplasty ring is implanted once and can never be adjusted. In ischemic MR, studies approximate that 20% of the surgical population will have re-occurring MR within the first year post surgery. These patients are typically a high risk to operate on so they are left to improvements in medical therapies which were not successful in the first place. Therefore, it would be advantageous to provide an annuloplasty ring where the shape and/or size of the ring could be adjusted to account for shape changes within the mitral valve. U.S. patent application Ser. No. 11/124,405, filed May 6, 2005, entitled "Adjustable Cardiac Valve Implant with Selective Dimensional Adjustment," incorporated herein in its entirety, discloses annuloplasty devices that can be adjusted within the body of a patient in a minimally invasive or non-invasive manner. Embodiments include annuloplasty rings constructed of a shape-memory material configured to transform from a first shape to a second shape in response to being heated. Thus, it would be advantageous to provide a device for delivering energy to portions of the implanted annuloplasty ring in vivo and thereby adjust the shape and/or size of the ring.

SUMMARY OF THE INVENTION

Thus, it would be advantageous to develop systems and methods for adjusting an implanted annuloplasty ring within the body of a patient in a minimally invasive or non-invasive manner.

In certain embodiments, an activation device, for applying energy to an implanted annuloplasty ring, is disclosed. The activation device comprises an outer elongate member having an outer elongate member distal end and an outer elongate member proximal end, and a lumen therebetween. The activation device further comprises an inner elongate member having a inner elongate member distal end and a inner elongate member proximal end, and a lumen therebetween, wherein the inner elongate member is slidably insertable through the lumen of the outer elongate member. The activation device comprises at least one adjustable spline having spline proximal and spline distal ends, the spline distal end connected to the inner tubular member distal end and the spline proximal end connected to the outer tubular member distal end, wherein the adjustable spline is configured to flex as the inner tubular member distal end is drawn proximally toward the outer tubular member distal end while the inner elongate member resides in the lumen of the outer elongate member. The activation device comprises at least one energy-transfer element coupled to the adjustable spline.

In certain embodiments, the at least one energy-transfer element comprises an electrode. In certain embodiments, a needle comprises the at least one energy-transfer element. In certain embodiments, the activation device further comprises a penetrating member that comprises the at least one energy-transfer element, the penetrating member being configured to penetrate an outer surface of the annuloplasty ring. In certain embodiments, the inner elongate member further comprises a distal tip positioned at the inner elongate member distal end and wherein the spline distal end is coupled to the distal tip. In certain embodiments, the activation device further comprises a plurality of splines defining a spine-group diameter, said spline-group diameter being a largest diameter of a curved closed shape that is intersected by said plurality of spines, and further comprises a wire extending proximally from the distal end of the plurality of splines, the wire configured to facilitate adjustment of a size of the spine-group diameter. In certain embodiments, the activation device further comprises at least one ring electrode, located in or on the at least one adjustable spline. In certain embodiments, the ring electrode is configured to provide electrocardiographic monitoring. In certain embodiments, the ring electrode is configured to monitor an impedance in adjacent body tissue. In certain embodiments, the activation further comprises at least one tip electrode, wherein the at least one tip electrode is located at the distal end of the inner tubular member, and wherein the distal tip of the inner tubular member is dimensioned to be positioned in a patient's left ventricle during use. In certain embodiments, the tip electrode is configured to provide electrocardiographic monitoring of the left ventricle. In certain embodiments, the tip electrode is configured to monitor an impedance in the left ventricle.

In certain embodiments, an activation device for applying energy to an implanted annuloplasty ring is disclosed. The activation device comprises an elongate member having a distal end, a proximal end and a lumen therebetween, the elongate member configured to be placed at least partially into an atrium of a patient's heart. The activation device further comprises first and second grasper jaws, each having inner and outer surfaces, coupled to the distal end of the elongate member, wherein the first and second grasper jaws are configured to be positioned around an object in an open position and to clamp on to the object, located between the inner surfaces of the first and second grasper jaws, in a closed position. The activation device further comprises an actuator configured to open and close the first and second graspers jaw, wherein the actuator is located at the proximal end of the elongate member. The activation device further comprises at least one energy-transfer element coupled to at least one of the inner surface of the first grasper jaw and the inner surface of the second grasper jaw, the at least one energy-transfer element being configured to deliver energy to an implanted cardiac implant, resulting in a change in a shape of the implant.

In certain embodiments, the at least one energy-transfer element comprises an electrode. In certain embodiments, a needle comprises the at least one energy-transfer element.

In certain embodiments, a method, for applying energy to an implanted annuloplasty ring, is disclosed. The method comprises providing an activation device. The activation device comprises an outer elongate member having an outer elongate member distal end and an outer elongate member proximal end, and a lumen therebetween. The activation device further comprises an inner elongate member having a inner elongate member distal end and a inner elongate member proximal end, and a lumen therebetween, wherein the inner elongate member is slidably insertable through the lumen of the outer elongate member. The activation device comprises at least one adjustable spline having spline proximal and spline distal ends, the spline distal end connected to the inner tubular member distal end and the spline proximal end connected to the outer tubular member distal end, wherein the adjustable spline is configured to flex as the inner tubular member distal end is drawn proximally toward the outer tubular member distal end while the inner elongate member resides in the lumen of the outer elongate member. The activation device comprises at least one energy-transfer element coupled to the adjustable spline. The method further comprises inserting the outer elongate member distal end, inner elongate member distal end, and the spline distal end into an atrium of a patient's heart at or near a base of an atrioventricular valve. The method further comprises engaging the activation device to the adjustable annuloplasty ring. The method further comprises applying energy from the at least one energy-transfer element to the adjustable annuloplasty ring.

In certain embodiments, the energy is selected from the group consisting of radiofrequency energy, mechanical energy, acoustic energy and electromagnetic energy. In certain embodiments, engaging the activation device to the adjustable annuloplasty ring comprises at least a portion of the at least one adjustable spline of the activation device contacting at least a portion of the adjustable annuloplasty ring. In certain embodiments, activating the adjustable annuloplasty ring comprises providing the energy to the adjustable annuloplasty ring. In certain embodiments, the energy is selected from the group consisting of radiofrequency energy, mechanical energy, acoustic energy and electromagnetic energy.

In certain embodiments, an activation device for applying energy to an implanted annuloplasty ring, is disclosed. The activation device comprises means for engaging an adjustable annuloplasty ring. The activation device further comprises means for applying an energy to the adjustable annuloplasty ring, the means for applying energy coupled to the means for engaging. The activation device further comprises means for actuating configured to act on the means for engaging, resulting in a widening in a diameter of the means for engaging, thereby facilitating engagement of the means for engaging to the adjustable annuloplasty ring.

For purposes of summarizing the invention, certain aspects, advantages, and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

DETAILED DESCRIPTION OF EXEMPLARY EMBODIMENTS

Figure 1:
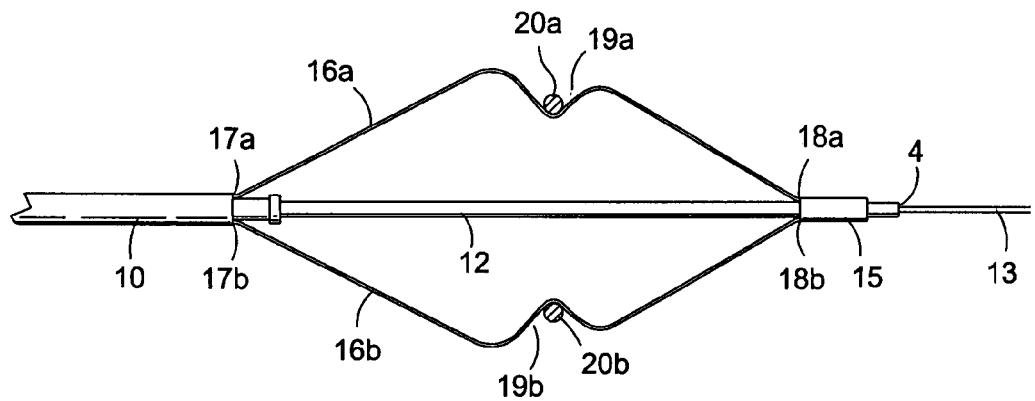
FIG. 1 depicts an embodiment of activation catheter according to the present invention.

The present invention involves systems and methods for reinforcing dysfunctional heart valves and other body structures with adjustable rings. In certain embodiments, an adjustable annuloplasty ring is implanted into the body of a patient such as a human or other animal. The adjustable annuloplasty ring is implanted through an incision or body opening either thoracically (e.g., open-heart surgery) or percutaneously (e.g., via a femoral artery or vein, or other arteries or veins) as is known to someone skilled in the art. The adjustable annuloplasty ring is attached to the annulus of a heart valve to improve leaflet coaptation and to reduce regurgitation. The annuloplasty ring may be selected from one or more shapes comprising a round or circular shape, an oval shape, a C-shape, a D-shape, a U-shape, an open circle shape, an open oval shape, and other curvilinear shapes. In one embodiment, a C-shape ring may be implanted at the mitral annulus to reduce mitral valve regurgitation (MR) or correct mitral valve insufficiency The size of the annuloplasty ring can be adjusted postoperatively to compensate for changes in the size of the heart. As used herein, "postoperatively" refers to a time after the adjustable annuloplasty ring is implanted and the body opening through which the adjustable annuloplasty ring was introduced into the patient's body is closed. For example, the annuloplasty ring may be implanted in a child whose heart grows as the child gets older. Thus, the size of the annuloplasty ring may need to be increased. As another example, the size of an enlarged heart may start to return to its normal size after an annuloplasty ring is implanted. Thus, the size of the annuloplasty ring may need to be decreased postoperatively to continue to reinforce the heart valve annulus.

In certain embodiments, the annuloplasty ring comprises a shape memory material that is responsive to changes in temperature and/or exposure to a magnetic field. Shape memory is the ability of a material to regain its shape after deformation. Shape memory materials include polymers, metals, metal alloys and ferromagnetic alloys. The annuloplasty ring is adjusted in vivo by applying an energy source to activate the shape memory material and cause it to change to a memorized shape. The energy source may include, for example, thermal energy, radio frequency (RF) energy, x-ray energy, microwave energy, ultrasonic energy such as focused ultrasound, high intensity focused ultrasound (HIFU) energy, light energy, electric field energy, magnetic field energy, combinations of the foregoing, or the like. For example, one embodiment of electromagnetic radiation that is useful is infrared energy having a wavelength in a range between approximately 750 nanometers and approximately 1600 nanometers. This type of infrared radiation may be produced efficiently by a solid state diode laser. In certain embodiments, the annuloplasty ring implant is selectively heated using short pulses of energy having an on and off period between each cycle. The energy pulses provide segmental heating which allows segmental adjustment of portions of the annuloplasty ring without adjusting the entire implant.

As discussed above, shape memory materials include, for example, polymers, metals, and metal alloys including ferromagnetic alloys. Exemplary shape memory polymers that are usable for certain embodiments of the present invention are disclosed by Langer, et al. in U.S. Pat. No. 6,720,402, issued Apr. 13, 2004, U.S. Pat. No. 6,388,043, issued May 14, 2002, and U.S. Pat. No. 6,160,084, issued Dec. 12, 2000, each of which are hereby incorporated by reference herein. Shape memory polymers respond to changes in temperature by changing to one or more permanent or memorized shapes. In certain embodiments, the shape memory polymer is heated to a temperature between approximately 38 degrees Celsius and approximately 60 degrees Celsius. In certain other embodiments, the shape memory polymer is heated to a temperature in a range between approximately 40 degrees Celsius and approximately 55 degrees Celsius. In certain embodiments, the shape memory polymer has a two-way shape memory effect wherein the shape memory polymer is heated to change it to a first memorized shape and cooled to change it to a second memorized shape. The shape memory polymer can be cooled, for example, by inserting or circulating a cooled fluid through a catheter.

Shape memory polymers implanted in a patient's body can be heated non-invasively using, for example, external light energy sources such as infrared, near-infrared, ultraviolet, microwave and/or visible light sources. In certain embodiments, the light energy is selected to increase absorption by the shape memory polymer and reduce absorption by the surrounding tissue. Thus, damage to the tissue surrounding the shape memory polymer is reduced when the shape memory polymer is heated to change its shape. In other embodiments, the shape memory polymer comprises gas bubbles or bubble containing liquids such as fluorocarbons and is heated by inducing a cavitation effect in the gas/liquid when exposed to HIFU energy. In other embodiments, the shape memory polymer may be heated using electromagnetic fields and may be coated with a material that absorbs electromagnetic fields.

Certain metal alloys have shape memory qualities and respond to changes in temperature and/or exposure to magnetic fields. Exemplary shape memory alloys that respond to changes in temperature include titanium-nickel, copper-zinc-aluminum, copper-aluminum-nickel, iron-manganese-silicon, iron-nickel-aluminum, gold-cadmium, combinations of the foregoing, and the like. In certain embodiments, the shape memory alloy comprises a biocompatible material such as a titanium-nickel alloy.

Shape memory alloys exist in two distinct solid phases called martensite and austenite. The martensite phase is relatively soft and easily deformed, whereas the austenite phase is relatively stronger and less easily deformed. For example, shape memory alloys enter the austenite phase at a relatively high temperature and the martensite phase at a relatively low temperature. Shape memory alloys begin transforming to the martensite phase at a start temperature ($M_s$) and finish transforming to the martensite phase at a finish temperature ($M_f$). Similarly, such shape memory alloys begin transforming to the austenite phase at a start temperature ($A_s$) and finish transforming to the austenite phase at a finish temperature ($A_f$). Both transformations have a hysteresis. Thus, the $M_s$ temperature and the $A_f$ temperature are not coincident with each other, and the $M_f$ temperature and the $A_s$ temperature are not coincident with each other.

In certain embodiments, the shape memory alloy is processed to form a memorized shape in the austenite phase in the form of a ring or partial ring. The shape memory alloy is then cooled below the $M_f$ temperature to enter the martensite phase and deformed into a larger or smaller ring. For example, in certain embodiments, the shape memory alloy is formed into a ring or partial ring that is larger than the memorized shape but still small enough to improve leaflet coaptation and reduce regurgitation in a heart valve upon being attached to the heart valve annulus. In certain such embodiments, the shape memory alloy is sufficiently malleable in the martensite phase to allow a user such as a physician to adjust the circumference of the ring in the martensite phase by hand to achieve a desired fit for a particular heart valve annulus. After the ring is attached to the heart valve annulus, the circumference of the ring can be adjusted non-invasively by heating the shape memory alloy to an activation temperature (e.g., temperatures ranging from the $A_s$ temperature to the $A_f$ temperature).

Thereafter, when the shape memory alloy is exposed to a temperature elevation and transformed to the austenite phase, the alloy changes in shape from the deformed shape to the memorized shape. Activation temperatures at which the shape memory alloy causes the shape of the annuloplasty ring to change shape can be selected and built into the annuloplasty ring such that collateral damage is reduced or eliminated in tissue adjacent the annuloplasty ring during the activation process. Exemplary $A_f$ temperatures for suitable shape memory alloys range between approximately 45 degrees Celsius and approximately 70 degrees Celsius. Furthermore, exemplary $M_s$ temperatures range between approximately 10 degrees Celsius and approximately 20 degrees Celsius, and exemplary $M_f$ temperatures range between approximately −1 degrees Celsius and approximately 15 degrees Celsius. The size of the annuloplasty ring can be changed all at once or incrementally in small steps at different times in order to achieve the adjustment necessary to produce the desired clinical result.

Certain shape memory alloys may further include a rhombohedral phase, having a rhombohedral start temperature ($R_s$) and a rhombohedral finish temperature ($R_f$), that exists between the austenite and martensite phases. An example of such a shape memory alloy is a NiTi alloy, which is commercially available from Memory Corporation (Bethel, Conn.). In certain embodiments, an exemplary $R_s$ temperature range is between approximately 30 degrees Celsius and approximately 50 degrees Celsius, and an exemplary $R_f$ temperature range is between approximately 20 degrees Celsius and approximately 35 degrees Celsius. One benefit of using a shape memory material having a rhombohedral phase is that in the rhomobohedral phase the shape memory material may experience a partial physical distortion, as compared to the generally rigid structure of the austenite phase and the generally deformable structure of the martensite phase.

Certain shape memory alloys exhibit a ferromagnetic shape memory effect wherein the shape memory alloy transforms from the martensite phase to the austenite phase when exposed to an external magnetic field. The term "ferromagnetic" as used herein is a broad term and is used in its ordinary sense and includes, without limitation, any material that easily magnetizes, such as a material having atoms that orient their electron spins to conform to an external magnetic field. Ferromagnetic materials include permanent magnets, which can be magnetized through a variety of modes, and materials, such as metals, that are attracted to permanent magnets. Ferromagnetic materials also include electromagnetic materials that are capable of being activated by an electromagnetic transmitter, such as one located outside the heart. Furthermore, ferromagnetic materials may include one or more polymer-bonded magnets, wherein magnetic particles are bound within a polymer matrix, such as a biocompatible polymer. The magnetic materials can comprise isotropic and/or anisotropic materials, such as for example NdFeB (Neodynium Iron Boron), SmCo (Samarium Cobalt), ferrite and/or AlNiCo (Aluminum Nickel Cobalt) particles.

Thus, an annuloplasty ring comprising a ferromagnetic shape memory alloy can be implanted in a first configuration having a first shape and later changed to a second configuration having a second (e.g., memorized) shape without heating the shape memory material above the $A_s$ temperature. Advantageously, nearby healthy tissue is not exposed to high temperatures that could damage the tissue. Further, since the ferromagnetic shape memory alloy does not need to be heated, the size of the annuloplasty ring can be adjusted more quickly and more uniformly than by heat activation.

Exemplary ferromagnetic shape memory alloys include Fe—C, Fe—Pd, Fe—Mn—Si, Co—Mn, Fe—Co—Ni—Ti, Ni—Mn—Ga, $Ni_2MnGa$, Co—Ni—Al, and the like. Certain of these shape memory materials may also change shape in response to changes in temperature. Thus, the shape of such materials can be adjusted by exposure to a magnetic field, by changing the temperature of the material, or both.

In certain embodiments, combinations of different shape memory materials are used. For example, annuloplasty rings according to certain embodiments comprise a combination of shape memory polymer and shape memory alloy (e.g., NiTi). In certain such embodiments, an annuloplasty ring comprises a shape memory polymer tube and a shape memory alloy (e.g., NiTi) disposed within the tube. Such embodiments are flexible and allow the size and shape of the shape memory to be further reduced without impacting fatigue properties. In addition, or in other embodiments, shape memory polymers are used with shape memory alloys to create a bi-directional (e.g., capable of expanding and contracting) annuloplasty ring. Bi-directional annuloplasty rings can be created with a wide variety of shape memory material combinations having different characteristics.

In certain embodiments, the annuloplasty ring will be made in the mitral annulus ring position. The current idea is to expand the "C" shaped ring at the mitral annulus. Post surgery, the implanted "C" ring can be manipulated in vivo by applying an energy source to one or more locations on the implant to activate the shape-memory material and cause it to change to a memorized shape. The re-shaping can take a number of different forms, so the energy will typically need to be applied at more than one location.

In certain embodiments, and as disclosed herein, the energy source can be surgically applied after the annuloplasty ring has been implanted by percutaneously inserting a catheter into the patient's body and applying the energy through the catheter. Certain embodiments of the catheter as described herein may be used to surgically apply the energy source. For example, RF energy, light energy or thermal energy (e.g., from a heating element using resistance heating) can be transferred to the shape memory material through a catheter positioned on or near the shape memory material. In certain embodiments, thermal energy can be provided to the shape memory material by injecting a heated fluid through a catheter or circulating the heated fluid in a balloon through the catheter placed in close proximity to the shape memory material. In certain embodiments, the energy source is applied surgically either during implantation or at a later time. For example, the shape memory material can be heated during implantation of the annuloplasty ring by touching the annuloplasty ring with warm object. As another example, the shape memory material can be coated with a photodynamic absorbing material which is activated to heat the shape memory material when illuminated by light from a laser diode or directed to the coating through fiber optic elements in a catheter. In certain such embodiments, the photodynamic absorbing material includes one or more drugs that are released when illuminated by the laser light.

In the following description, reference is made to the accompanying drawings, which form a part hereof, and which show, by way of illustration, specific embodiments or processes in which the invention may be practiced. Where possible, the same reference numbers are used throughout the drawings to refer to the same or like components. In some instances, numerous specific details are set forth in order to provide a thorough understanding of the present disclosure. The present disclosure, however, may be practiced without the specific details or with certain alternative equivalent components and methods to those described herein. In other instances, well-known components and methods have not been described in detail so as not to unnecessarily obscure aspects of the present disclosure.

FIG. 1 illustrates an embodiment of the activation catheter having an outer tube 10 including a lumen 11 and an inner tube 12 slidably insertable through the lumen 11 of the outer tube 10. The inner tube may have a guidewire lumen 13 extending along the longitudinal axis and a tip 15 located on the distal end. One or more expandable splines 16a-b may be connected at a first connection point 17a-b along the circumference of the distal end of the outer tube and at a second connection point 18a-b along the circumference of the distal tip of the inner tub. As used herein, a "spline" is a length of material, usually, but not always, greater in length than width, such as a relatively long strip or cord of the material, the strip or cord being relatively fixed in position at a number of points, and the strip relaxing to form a curve, sometimes a relatively smooth curve, passing through those points. In certain embodiments, the activation catheter may include two splines. In certain embodiments, the activation catheter may include any number of additional splines to further facilitate positioning the device near the implanted annuloplasty ring and to provide additional stability during delivery of RF energy to the ring by minimizing tilting of the device once it is engaged. For example, in certain embodiments, the catheter may have three splines. In certain embodiments, the catheter may have four splines. In certain embodiments, the catheter may have five splines. In certain embodiments, the catheter may have six splines. In certain embodiments, the catheter may have seven splines. In certain embodiments, the catheter may have eight splines. In certain embodiments, the catheter may have any suitable number of splines for contacting positioning along an implanted annuloplasty ring. In certain embodiments, the one or more splines may be constructed of a flexible shape-memory material, such as a nitinol wire shape or any other suitable shape-memory material, such that when the inner tube is pulled proximally back through the lumen of the outer tube, the spline will bow out and expand in diameter. As used herein, the term "wire" is a broad term having at least its ordinary and customary meaning and includes, for example, solid, hollow or tubular elongated structures having a cross-section having a variety of shapes, including shapes that are curvilinear, rectilinear, circular, elliptical. In certain embodiments, when the inner tube is advanced distally beyond the distal end of the outer tube, the spline will contract and be reduced in diameter. In certain embodiments, the spline(s) are made of a pseudoelastic shape-memory material such that when the spline is bowed out, i.e. the longitudinal tension on the spline is released, the spline transforms back to its original shape having a dimple 19a-b in the intermediate region of the spline.

In certain embodiments, during use the inner tube 11 can be pulled proximally to expand the cross-sectional diameter (span) of the spline(s) 16a-b and engage the implanted annuloplasty ring. The annuloplasty ring will dock with dimple(s) 19a-b on the spline(s) 16a-b to maintain contact and hold the splines 16a-b steady during the procedure. The spline(s) 16a-b may range in length and may be contracted as much as necessary to provide the appropriate cross sectional diameter in the dimpled area 19a-b to engage the implanted annuloplasty ring. In certain embodiments, the length of the spline is selected to provide for a maximum range of cross-sectional diameters to accommodate a wide range of sizes of annuloplasty rings while minimizing the length of the catheter that must be initially advanced through the left ventricle to deliver the fully extended splines.

Figure 2:
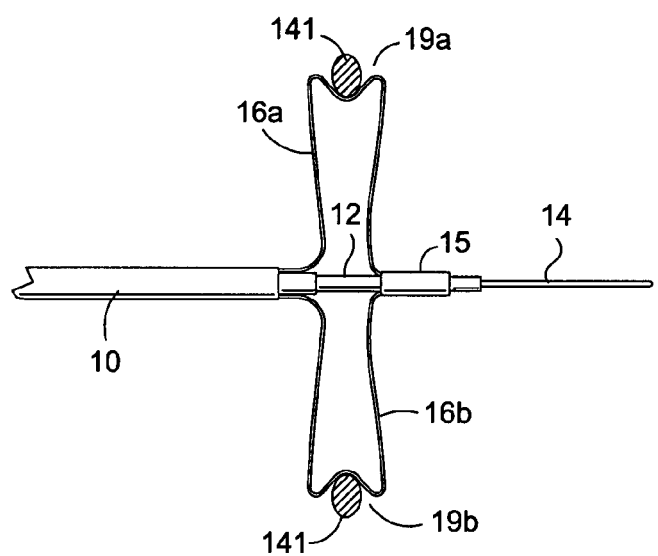
FIG. 2 depicts an alternative embodiment of activation catheter according to the present invention.
Figure 3:
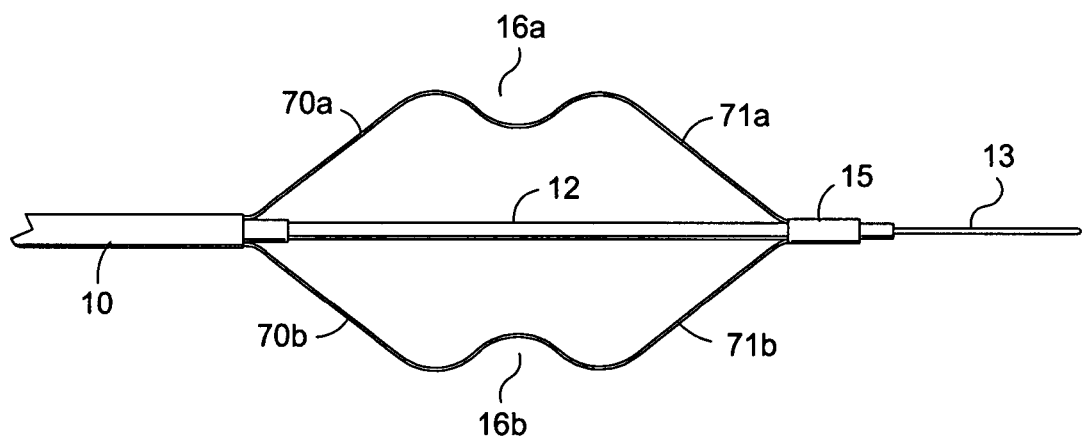
FIG. 3 depicts an alternative embodiment of activation catheter according to the present invention.

FIGS. 2 and 3 depict alternative configurations for the shaped memory splines. For example, in FIG. 2, the splines 16a-b when fully expanded to engage the implanted annuloplasty ring 141, form a single narrow loop with a groove or dimpled area 19a-b located at the apex of the loop. FIG. 3 depicts splines 16a-b having two uniform diameter bulges 30a-b and 31a-b with a dimpled region 19a-b located in between. It is envisioned, that for varying diameter rings, one or more of the alternate designs may advantageously provide the ability to increase the diameter of the spline in its expanded state, to correspond with a larger diameter ring, while minimizing the length of the catheter that must be advanced into the left ventricle when the spline is in an unexpanded state.

Figure 4:
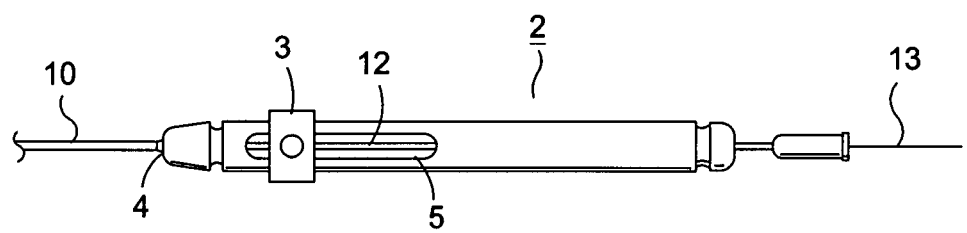
FIG. 4 depicts a handle for use with an activation catheter according to the present invention.

In certain embodiments, once the spline has been sufficiently contracted to engage the annuloplasty ring, the inner tube may be locked in place with respect to the outer tube such that the diameter of the spline cannot shift. The transverse force of the ring applied to the ring in the dimpled region may then effectively anchor the spline against the ring. As shown in FIG. 4, a handle 2 may be connected to the outer tube 10 for controlling and locking movement of the inner tube 12 with respect to the outer tube 10. The handle may be fixedly attached to the proximal end of the outer tube 10 such that the aperture of the outer tube 10 is aligned with a lumen 4 in the handle 2. The proximal end of the inner tube 12 may extend through the lumen 4 of the handle. The inner tube 12 may further be engaged by a slidably knob 3 extending though a longitudinal opening 5 in the handle body. Thus, when the knob 3 is moved forward or back along the longitudinal opening, it moves the inner tube with respect to the outer tube to alternately extend or contract the spline(s). Once the desired position for the splines has been achieved, a screw 6 on the know 3 can be tightened to prevent the knob 3 from sliding along the opening and thus fix the position of the splines.

In certain embodiments, the spline(s) 16a-b further include one or more RF heating electrodes 20a-b mounted on the surface of the spline(s). In certain embodiments, the RF heating electrode(s) 20a-b can be mounted in the dimple(s) 19a-b. In certain embodiments, the electrode(s) may be positioned at any location along the surface of the spline that will contact the annuloplasty ring when the spline and ring are engaged. The RF heating electrodes 20a-b may be conductive strips, plates or wires embedded in or mounted on the spline, a conductive ring encircling a cross section of the spline or any other suitable conductor. In certain embodiments, the RF heating electrodes 20a-b can be electrically coupled to an RF generator or other suitable RF energy source.

In certain embodiments, once the spline(s) 16a-b are docked against the annuloplasty ring, the RF heating electrodes 20a-b may be activated to deliver RF energy to contact area on the annuloplasty ring and thereby heat a localized region of the annuloplasty ring. The RF heating electrodes 20a-b may further include a thermocouple sensor to measure the temperature at the contact site on the annuloplasty ring while the RF heating electrode is transmitting RF energy. The temperature sensor provides real-time feedback to the RF generator to regulate the delivery of RF energy to reach and maintain the desired temperature at the annuloplasty ring. For example, in certain embodiments, the RF generator compares the temperature information with the user defined set temperature for the contact site on the annuloplasty ring. Once the RF generator registers that the contact site is nearing or has reached the preset maximum temperature, the RF generator may decrease or completely stop delivering RF energy to the RF heating electrode.

Figure 5:
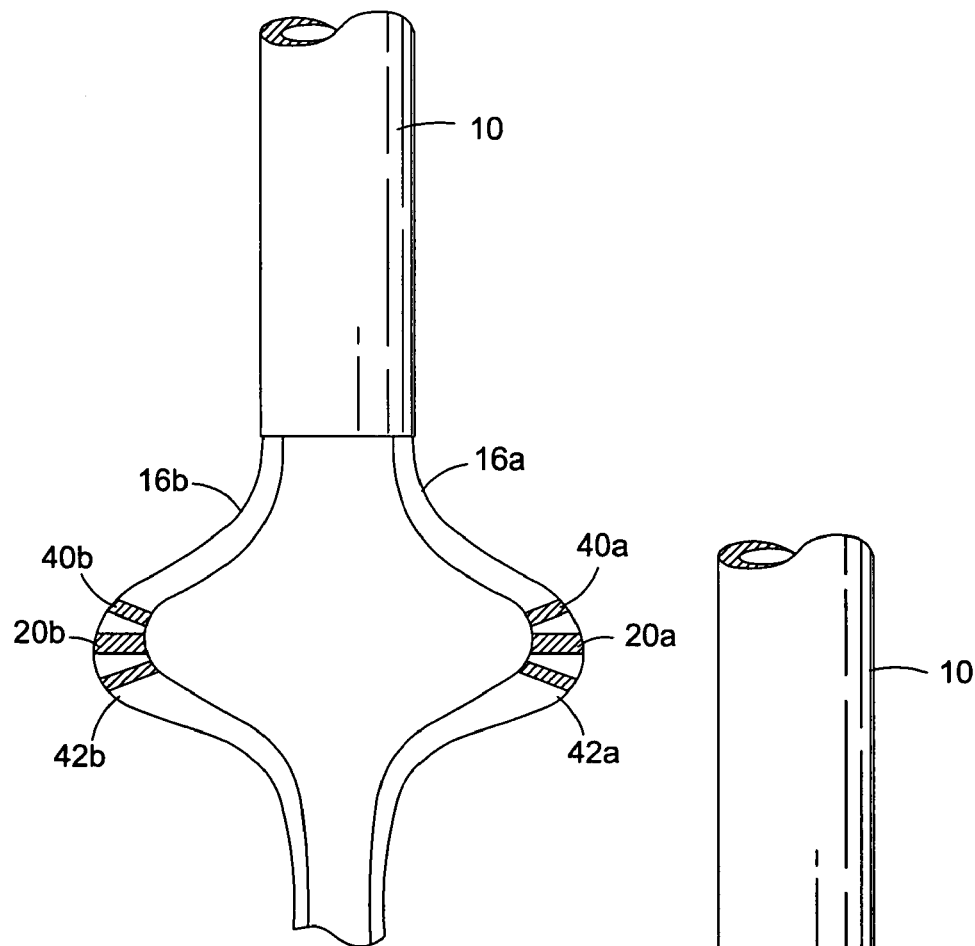
FIG. 5 depicts an alternative embodiment of activation catheter having a magnetic engagement mechanism.
Figure 6:
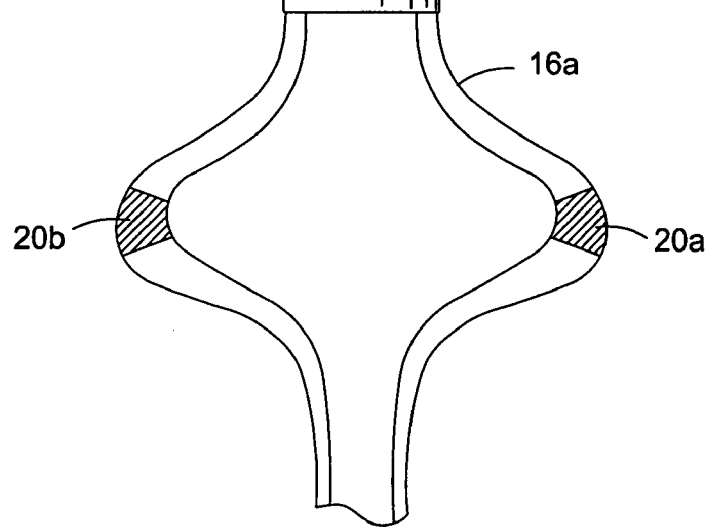
FIG. 6 depicts an alternative embodiment of activation catheter having magnetic electrodes.

In certain embodiments, as shown in FIGS. 5 and 6, the splines 16a-b may further include one or more magnets 40a-b, 42a-b mounted on the spline(s) proximal to the RF heating electrode(s). The magnet(s) 40a-b, 42a-b are configured to be aligned with a magnet of the opposite pole located on an implanted annuloplasty ring. Since the magnets 40a-b and 42a-b are of opposite poles, the interaction of their magnetic fields will cause the magnets of the activation catheter 40a-b, 42a-b and magnets located on an implanted annuloplasty ring to attract one another, thus firmly latching the spline to the annuloplasty ring and forming a tight connection to hold the RF heating electrode(s) 20a-b in place in the face of pressure forces from the heart. In certain embodiments, and as depicted in FIG. 6, the RF heating electrode(s) 20a-b may have magnetic properties such that, in use, the RF heating electrode(s) 20a-b may themselves be attracted to opposite pole magnets located on the implanted annuloplasty ring.

Figure 7:
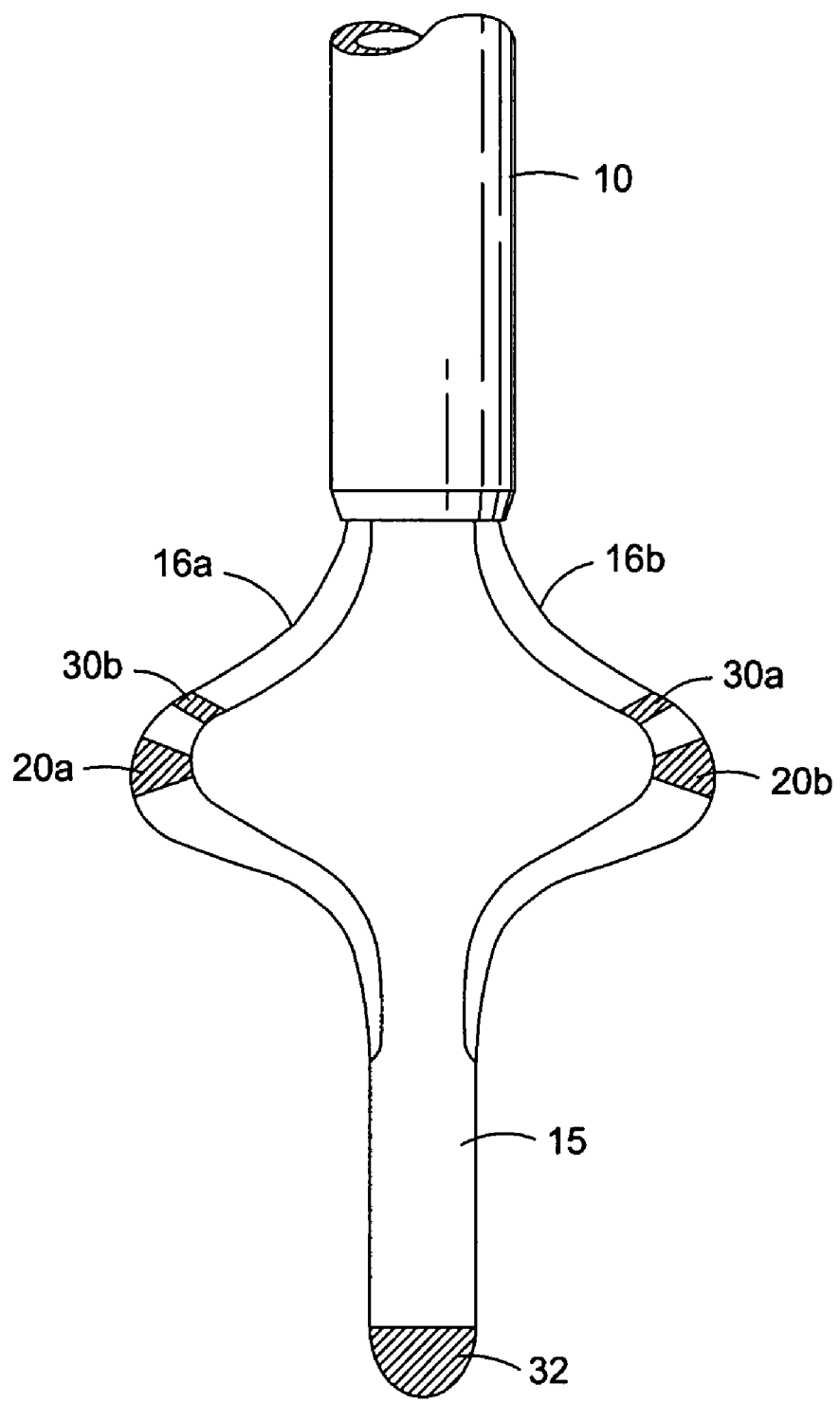
FIG. 7 depicts an alternative embodiment of activation catheter having an electrocardio monitoring system.

In certain embodiments, and as shown in FIG. 7, the splines 16a-b may further include one or more ring electrodes 30a-b for electrocardiogram monitoring. In certain embodiments, the ring electrode(s) 30a-b are mounted in or on the spline near the RF heating electrode(s) 20a-b such that the ring electrodes 30a-b may monitor local electrocardio activity of the heart while the RF heating electrode(s) 20a-b delivers RF energy to the annuloplasty ring. The ring electrode(s) 30a-b transmit can intercardiac electrogram signals, thereby providing continuous electrocardiogram monitoring. The electrogram signals may be used by the physician to monitor electrocardio activity of the heart and to ensure that the application of the RF energy to the annuloplasty ring is not creating any heart arrhythmias. In addition, certain changes in the electrogram signals may be monitored to determine whether the RF energy is damaging the surrounding tissue and to control the application of RF energy to minimize or avoid tissue damage from the RF energy. The ring electrode(s) 30a-b can further measure and relay the impedance as RF energy is applied to the annuloplasty ring. Increases in the impedance are also indicative of tissue damage, thus, measuring the impedance provides an additional mechanism for monitoring the surrounding tissue as RF energy is applied and for controlling the delivery of RF energy to avoid and/or minimize tissue damage.

In certain embodiments, the catheter may further have a tip electrode 32 mounted to the distal tip for providing electrocardiogram and impedance monitoring in the left ventricle. The tip electrode 32 may be mounted on the distal tip of the catheter. In use, when the splines are positioned near the implanted annuloplasty ring such that the RF heating electrodes 20a-b are aligned with the annuloplasty ring, the distal tip of the catheter may extend into the patient's left ventricle and monitor the electrocardio activity of the left ventricle while the RF energy is being applied. The electrogram signals from the left ventricle may be used by the physician to monitor electrocardio activity of the heart and to ensure that the application of the RF energy to the annuloplasty ring is not creating any heart arrhythmias and/or damaging tissue in the left ventricle. As with the ring electrode(s) 30a-b, the tip electrode 32 may further measure and relay the impedance as RF energy is applied to the annuloplasty ring providing an additional mechanism for monitoring the left ventricle as RF energy is applied and for controlling the delivery of RF energy to avoid and/or minimize tissue damage.

Figure 8:
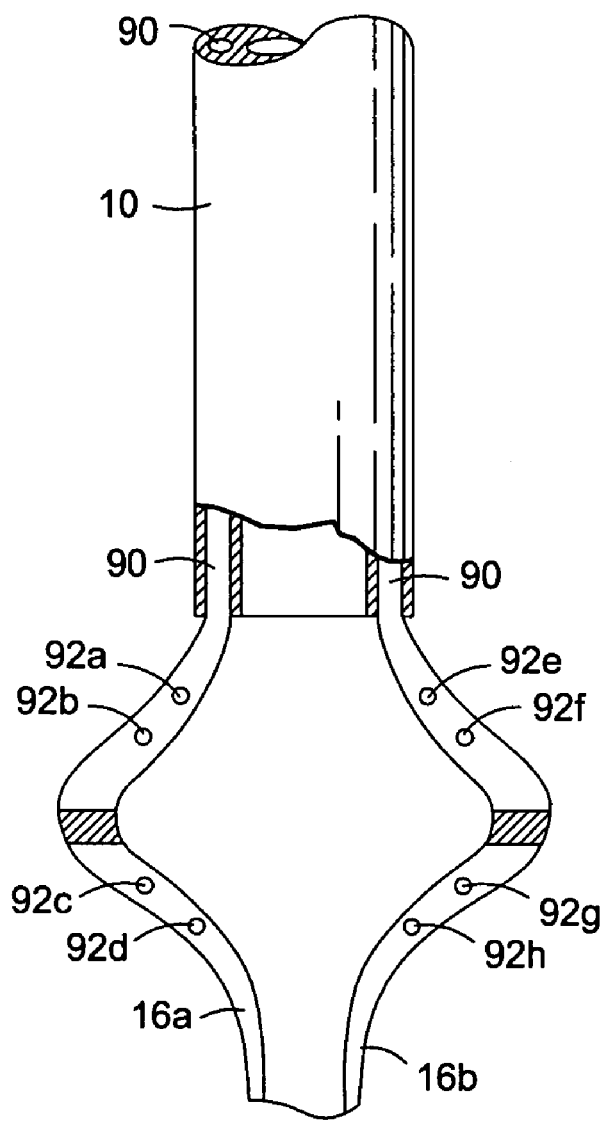
FIG. 8 depicts an alternative embodiment of activation catheter having a cooling system.
Figure 9:
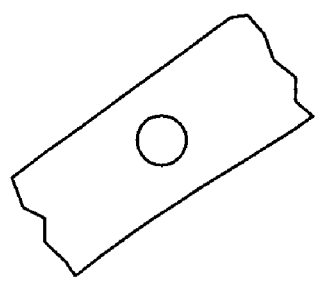
FIG. 9 depicts a top view of an irrigation and delivery hole of the catheter of FIG. 8.

In certain embodiments, the activation catheter may further include a cooling system whereby heparinized saline, or any other suitable cooled liquid, may be delivered to the tissue surrounding the implanted annuloplasty ring while the RF energy is being applied. As shown in FIGS. 8-9, the outer tube 10 may have an irrigation lumen 90 through which the cooled liquid may be delivered to the region while the RF energy is being applied to the implanted annuloplasty ring. The cooled liquid may assist in insulating the surrounding tissue from the heat of the RF energy and thereby minimize and/or avoid char formation and tissue damage in the surrounding tissue. In certain embodiments, the splines 16a-b may further include a plurality of irrigation holes 92a-h surrounding the RF heating electrodes 20a-b. In certain embodiments, the splines 16a-b have a lumen for delivering the cooled liquid or saline to the irrigation holes and to the tissue immediately surrounding the RF heating electrodes 20a-b. Flushing with cooled liquid may permit higher levels of RF energy to be applied to the annuloplasty ring to quickly raise the nitinol temperature without heating the tissue covering the surface of the implanted ring and/or surrounding the implanted ring.

Figure 10:
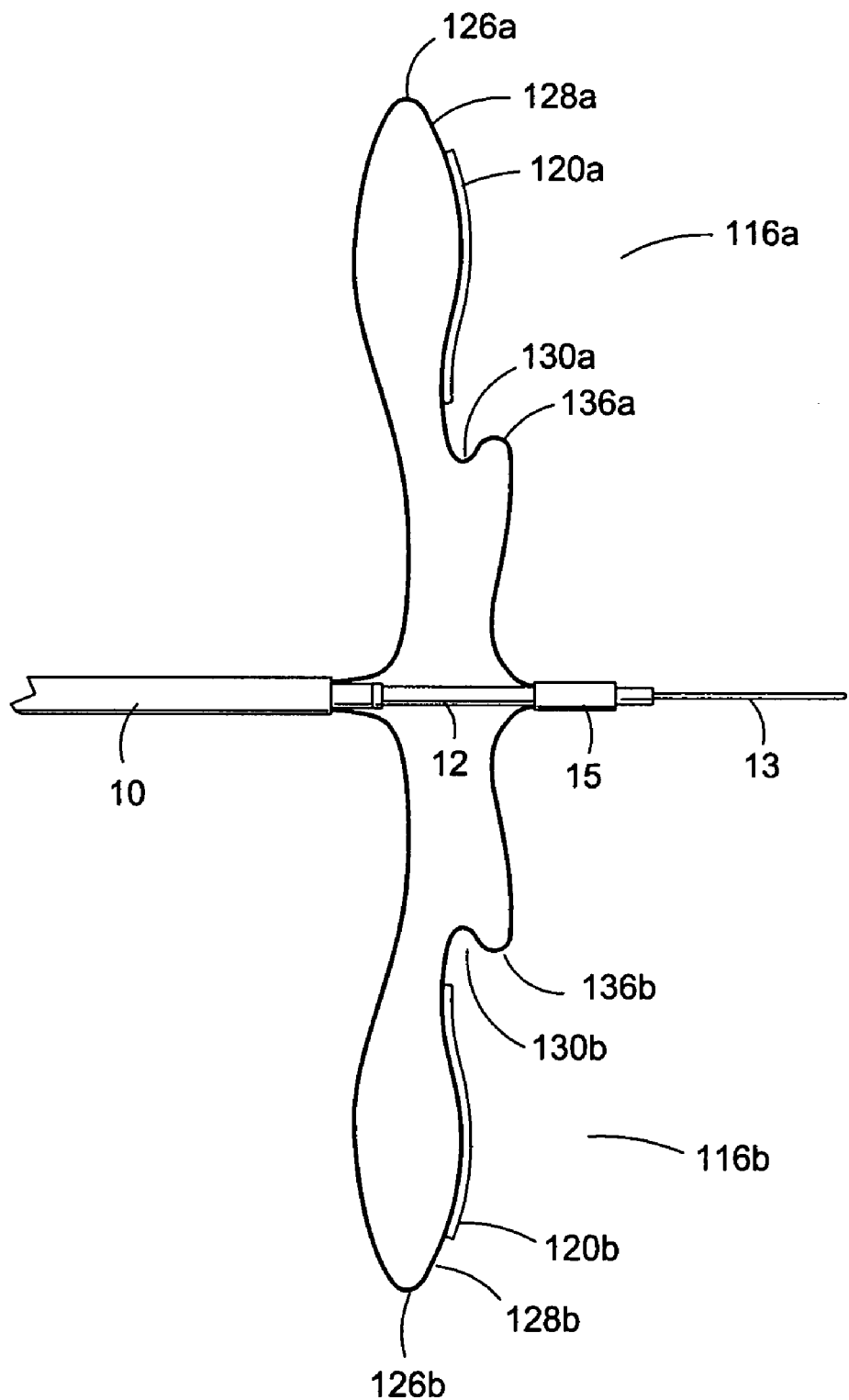
FIG. 10 depicts an alternative embodiment of activation catheter according to the present invention.

As shown in FIG. 10, the expandable splines may have alternative shapes. In FIG. 10, the splines 116a-b have a memory shape such that when the distal tip 13 is pulled proximally toward the outer tube 10 and the splines 116a-b are expanded, the splines 116a-b revert to a shape having a proximal bulge 126a-b and a smaller distal bulge 136a-b with a groove or notch 130a-b formed in between the bulges 126a-b and 136a-b. One or more RF heating electrodes 120a-120b may be mounted along the distal surface 128a-b of the proximal bulge 126a-b. The electrodes 120a-120b may further comprise a plurality of adjacent electrodes, or a conductive strip, plates or wire. In certain embodiments, the electrodes 120a-b extend over the length of the distal surface 128a-b of the proximal bulge 126a-b such that the annuloplasty ring 400 may engage the electrodes 120a-120b at any point on the distal surface 128a-b.

Figure 11:
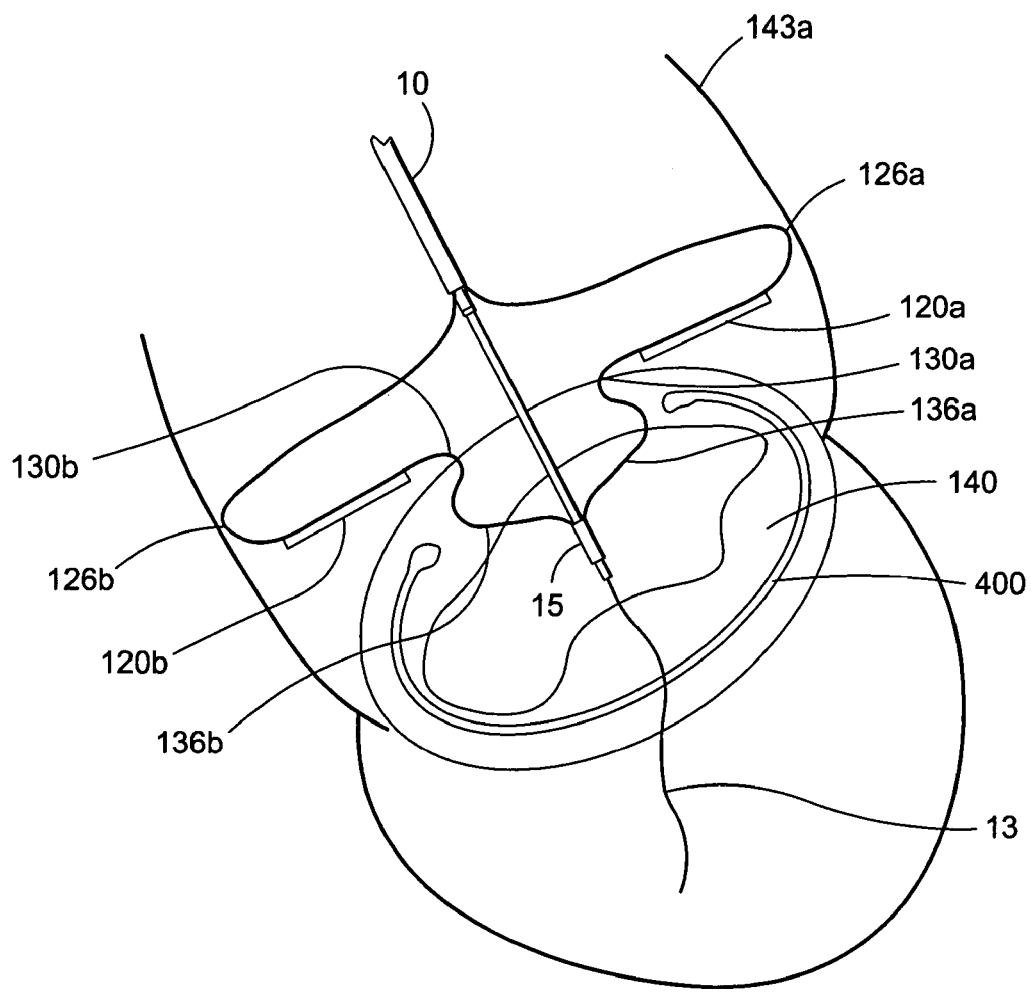
FIG. 11 depicts the catheter of FIG. 10 deployed in a patient's left atrium.

In use, as shown in FIG. 11 the distal tip 15 is retracted until the diameter of the proximal bulge 126a-b is sized to engage the wall of the patient's left atrium 143. The catheter may then be advanced, using the wall of the left atrium 143 as a guide, until the proximal bulge 126a-b is abutting the mitral valve 140 and the implanted annuloplasty ring 400. Here, the physician may engage the device with the annuloplasty ring 400 by applying constant force against the expanded splines in the direction of the annulus to keep the proximal bulge 126a-b firmly pressed against the annuloplasty ring 141. In certain embodiments, the smaller distal bulge 136a-b may be operatively sized to engage the annuloplasty ring 141 such that the annuloplasty ring may be caught in a groove or notch 130a-b formed at the intersection of the proximal and distal bulges 126a-b and 136a-b thereby creating a positive lock on the implanted ring. Here, the splines 116a-b would be held in position by both the longitudinal forces pressing the proximal bulge 126a-b against the left atrium 143 and the mitral valve 140 as well as the perpendicular forces of the groove 138a-b pressing against the engaged annuloplasty ring 400.

Figure 12:
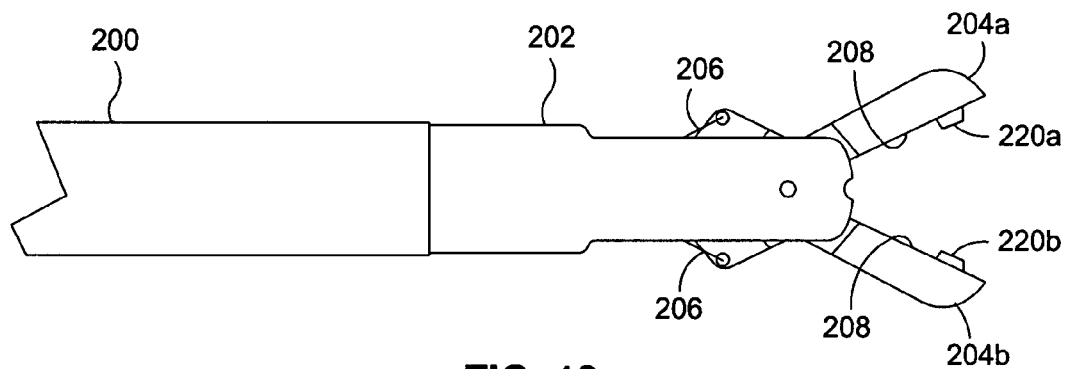
FIG. 12 depicts an alternative embodiment of activation catheter having a distal working tip with a grasper jaw for engaging an annuloplasty ring.

FIG. 12 depicts an alternative embodiment of an activation catheter having an elongate tubular member 200 and a distal tip 202 for engaging the implanted annuloplasty ring and delivering RF energy. The distal tip 202 has grasping jaws 204 mounted on the tip 202. The jaws 204 are attached to a wire 206 which extend through the lumen of the elongate tubular member and are accessible at the proximal end of the elongate tubular member for controlling the motion of the grasper jaws 204. One or more electrodes 220 are mounted on the inner surfaces 208 of the grasper jaws 204. The grasper catheter is advantageous in that it not limited to contacting and transferring energy to the annuloplasty ring at a finite number of locations. Rather since the grasper jaws 204 can be fully rotated and can clamp the ring at any location about the axis of rotation, the grasper jaws 204 have virtually an infinite number of positions for connecting with and transferring energy to the annuloplasty ring. In addition, certain embodiments may further include a plurality of electrodes along the wide, flat inner surfaces 208 of each grasper jaw such that the jaws may deliver RF energy to multiple locations once connected to the annuloplasty ring.

In use, a deflectable guide catheter may be positioned proximal to the implanted annuloplasty ring, adjacent to the desired location for applying RF energy using a guide catheter and methods known in the art. The grasper catheter may then be advanced through a lumen in the deflectable guide catheter until the distal tip 202 of the grasper catheter extends from the distal end of the guide catheter and is positioned proximal to a first location on the annuloplasty ring where RF energy is to be applied. The grasper catheter may be rotated until the jaws are aligned with the annuloplasty ring. The jaws 204 may be activated to open and surround the annuloplasty ring. Once the electrodes 220 on the inner surfaces 206 of the jaws have been property aligned with the annuloplasty ring, the jaws 204 may be activated to close and clamp down on the annuloplasty ring. In certain embodiments, RF energy may be applied to the annuloplasty ring via the electrodes 220 on the inner surfaces 208 of the jaws. The jaws 204 serve the dual purpose of providing RF energy via the attached electrodes 220 and locking on to the annuloplasty ring to maintain stability and positioning during the application of the RF energy. As discussed above in the previous embodiments, the RF heating electrodes 220 may further include a thermocouple sensor to measure the temperature at the contact site on the annuloplasty ring while the RF heating electrode is transmitting RF energy. Once the RF energy has been applied to the first location on the annuloplasty ring, the grasper jaws be activated to open and release the implanted annuloplasty ring and then withdrawn from the patient via the guide catheter lumen.

In certain embodiments, if it is desired to apply energy to additional locations along the circumference of the annuloplasty ring, the catheter may be withdrawn until the distal tip is positioned within the lumen of the deflectable guide catheter. The deflectable guide catheter may then be maneuvered proximal to a second location on the annuloplasty ring where RF energy is to be delivered using techniques known in the art. Once the deflectable guide catheter has been positioned proximal to the second location, the grasper catheter may be advanced through the guide catheter lumen until the distal tip 202 of the grasper catheter extends from the distal end of the guide catheter and is positioned proximal to the second location. The grasper catheter may be rotated until the jaws 204 are aligned with the annuloplasty ring. The jaws 204 may be activated to open and surround the annuloplasty ring. Once the electrodes 220 on the inner surfaces 208 of the jaws have been property aligned with the annuloplasty ring, the jaws 204 may be activated to close and clamp down on the annuloplasty ring. RF energy may be applied to the annuloplasty ring via the electrodes 220 on the inner surfaces 208 of the jaws. This process may be repeated as many times as desired to apply RF energy to multiple locations along the circumference of the implanted annuloplasty ring. Once RF energy has been applied to all desired locations, the grasper catheter may be withdrawn from the patient via the lumen of the guide catheter.

Figure 13:
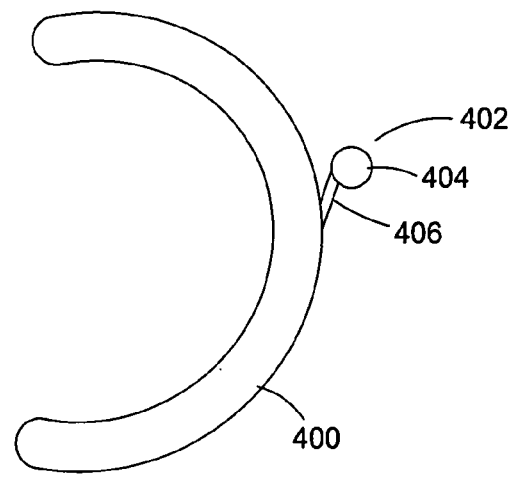
FIG. 13 depicts an annuloplasty ring having a mating feature.
Figure 14A:
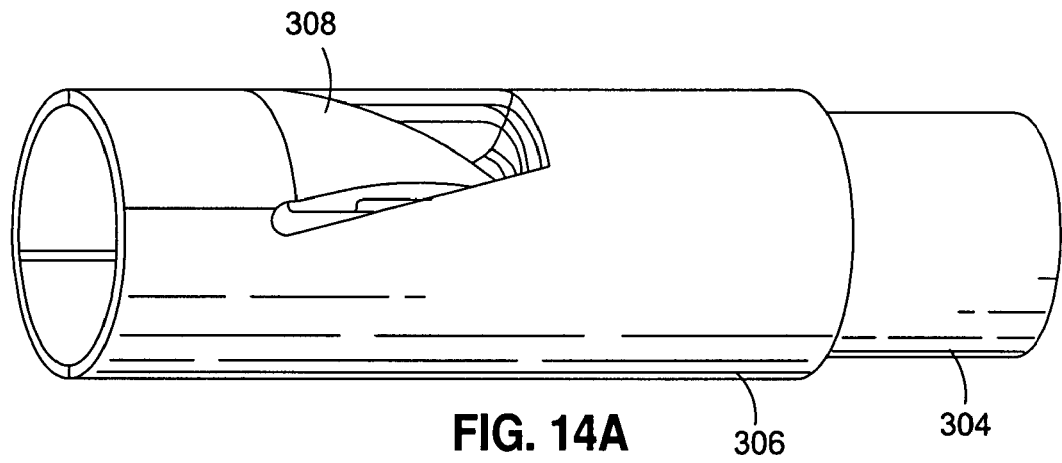
FIG. 14A depicts an alternative embodiment of activation catheter having a distal working tip having tabs for connecting with a protruding mating feature.
Figure 14B:
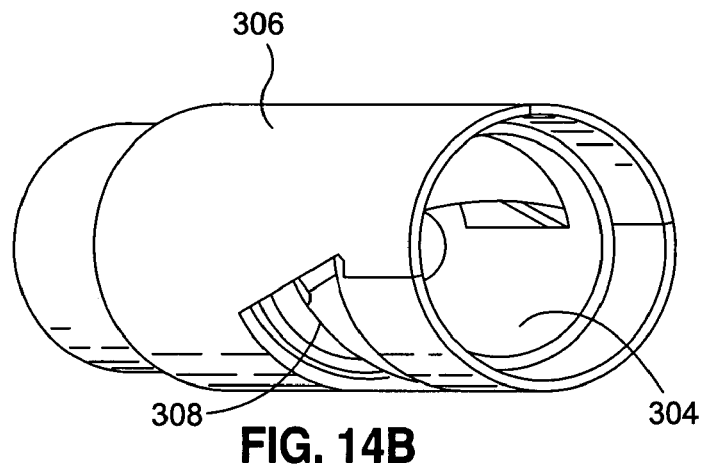
FIG. 14B depicts an alternative embodiment of activation catheter having a distal working tip having tabs for connecting with a protruding mating feature.
Figure 14C:
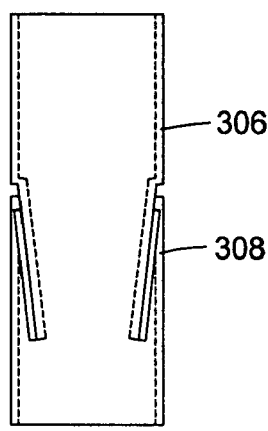
FIG. 14C depicts the outer hypotube of an activation catheter having tabs for connecting with a protruding mating feature.
Figure 14D:
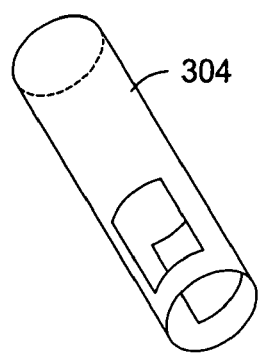
FIG. 14D depicts the inner hypotube of an activation catheter having tabs for connecting with a protruding mating feature.
Figure 14E:
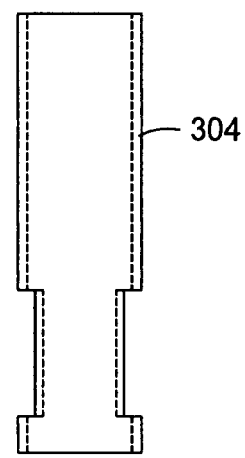
FIG. 14E depicts the inner hypotube of an activation catheter having tabs for connecting with a protruding mating feature.

FIGS. 14A-E depict an alternative embodiment of activation catheter having a distal working tip 302 having tabs 304 for connecting with a protruding mating feature on an implanted annuloplasty ring. As shown in FIG. 13, certain embodiments of the implanted annuloplasty ring 400 may include one or more mating feature 402, for example a post 406 and ball 404, spaced apart along the circumference of the ring and protruding transversely from the ring 400. In certain embodiments, the mating post is sized and configured to prevent tissue growth over the mating post. Thus, the mating post may provide target to which the activation catheter may on and deliver RF energy. As shown in FIGS. 14A-E, an embodiment of an activation catheter for use with such a mating post may include a distal working tip 302 having an inner tube 304 and an outer tube 306. The outer tube 306 may have one or more bent tabs 308 disposed around the circumference. Initially, the tabs 308 are bent inward and held in place by a locking mechanism on the inner tube 304. Once the catheter has been positioned near a mating feature 402 on the implanted annuloplasty ring 400, the tab(s) 308 may be deployed, for example by sliding the inner tube 304 relative to the outer tube 306 to release a locking mechanism. The tab(s) 308 may grasp the mating feature 302 to securely position the activation catheter with respect to the annuloplasty ring. In certain embodiments, the tab(s) 308 may further include RF heating electrodes 320 mounted on the outer surface of the tab(s) 308 such that when the tab(s) 308 are deployed and connect with the mating feature, RF energy may be delivered to the annuloplasty ring via the mating feature 402. In certain embodiments, the RF heating electrodes may comprise a semi radial band mounted along an inner diameter of the inner tube such that when the tab(s) 308 are deployed, the tab(s) 308 may engage the mating post 404 and position the ball 406 proximal to the inner opening in the inner tube formed by releasing the tab(s) 308. The RF energy may then be delivered to the annuloplasty ring via contact between the electrode and the ball 406 of the mating feature 402.

Figure 15A:
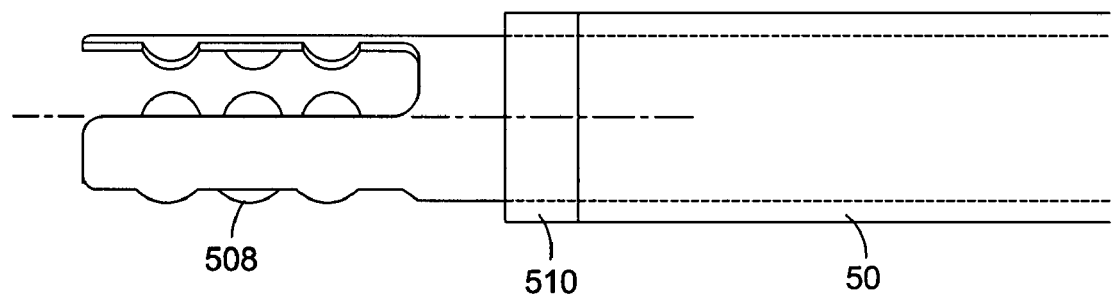
FIG. 15A depicts an alternative embodiment of an activation catheter having a distal working tip with fingers for engaging an annuloplasty ring.
Figure 15B:
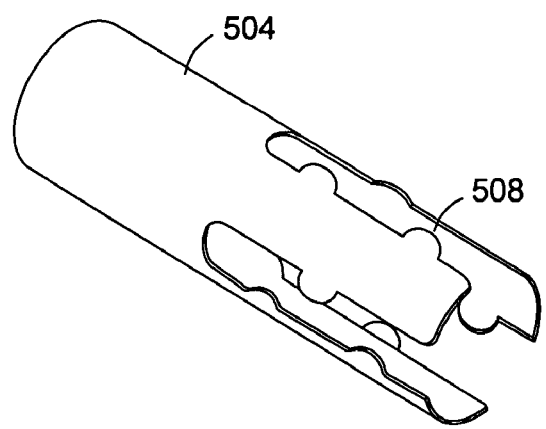
FIG. 15B depicts an alternative embodiment of an activation catheter having a distal working tip with fingers for engaging an annuloplasty ring.

FIGS. 15A-B depicts an alternative embodiment of an activation catheter for engaging a mating feature on the annuloplasty ring having a distal working tip 502 including an inner hypotube 504 slidably insertable in an outer hypotube 506. Here, the distal end of the inner hypotube includes one or more fingers or fringes 508. In certain embodiments, the fingers 508 may be layer cut in the wall of the inner tube. In certain embodiments, the fingers 508 may be connected to the distal end of the inner tube. In certain embodiments, the fingers 508 are made of shape set nitinol. Initially, the fingers 508 would be held in a closed configuration by the inner wall of the outer tube 506. In certain embodiments, the outer hypotube 508 may further include a band 510 located at the distal end for facilitating the opening and closing of the fingers 508. For example, in certain embodiments the fingers 508 may be placed under tension such that when the outer tube 506 is removed the fingers 508 may spring open.

In use, once the catheter is positioned near a mating feature 402 on the implanted annuloplasty ring 400, the outer tube 506 may be slid proximally to expose the distal end of the inner tube 504. The fingers 508 may be released and allowed to expand and surround the mating feature 402. One or more electrodes may be mounted on the fingers 508 such that when the fingers 508 engage the mating feature 402, the electrodes are placed in contact with the mating feature 402. In alternative embodiments, the activation catheter may be used on a ring 400 that does not have one or more mating features 402. Here, the fingers 508 may engage the implanted annuloplasty ring directly.

Figure 16:
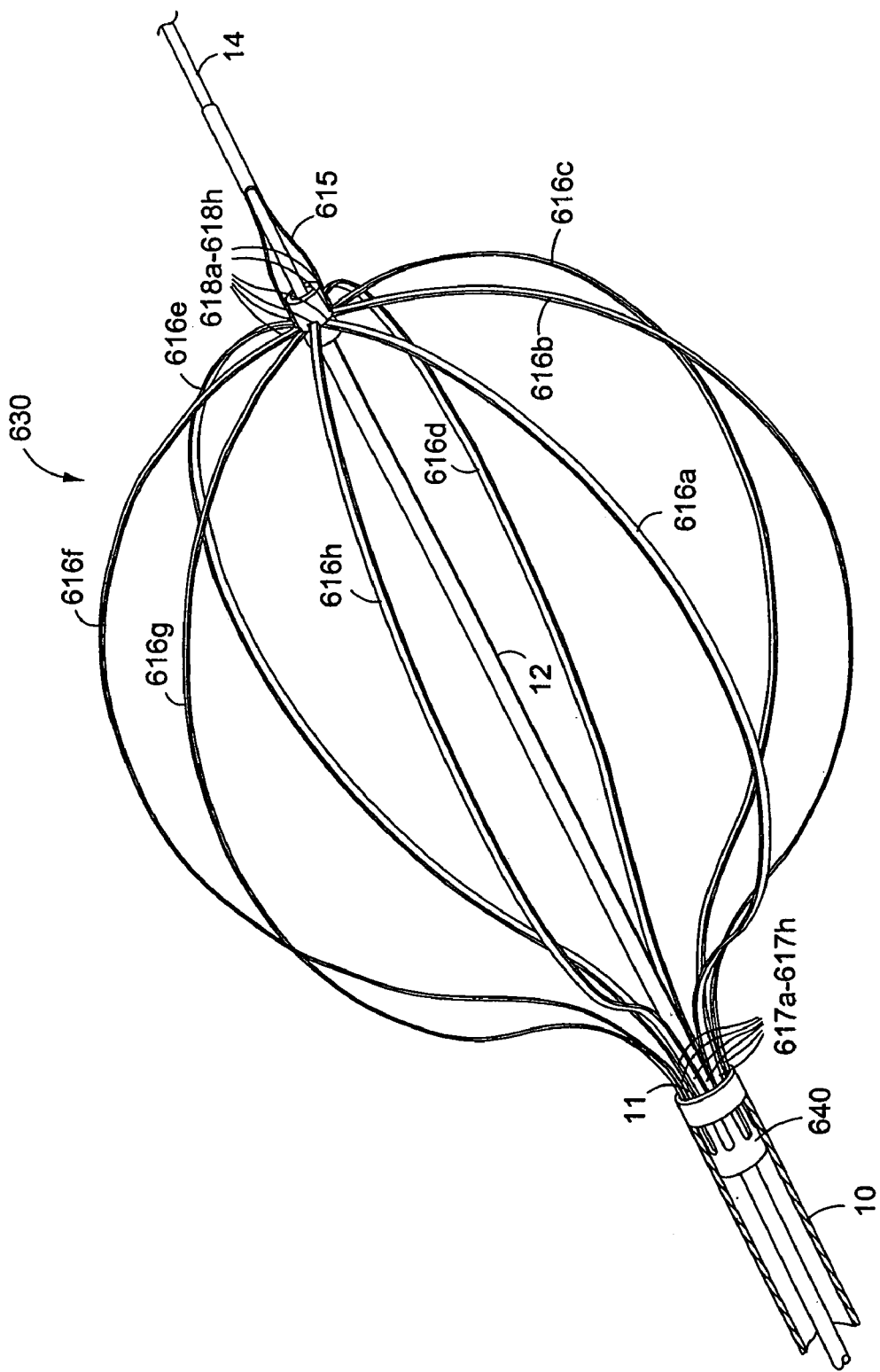
FIG. 16 depicts an alternative embodiment of activation catheter having a basket assembly for engaging an annuloplasty ring.
Figure 17:
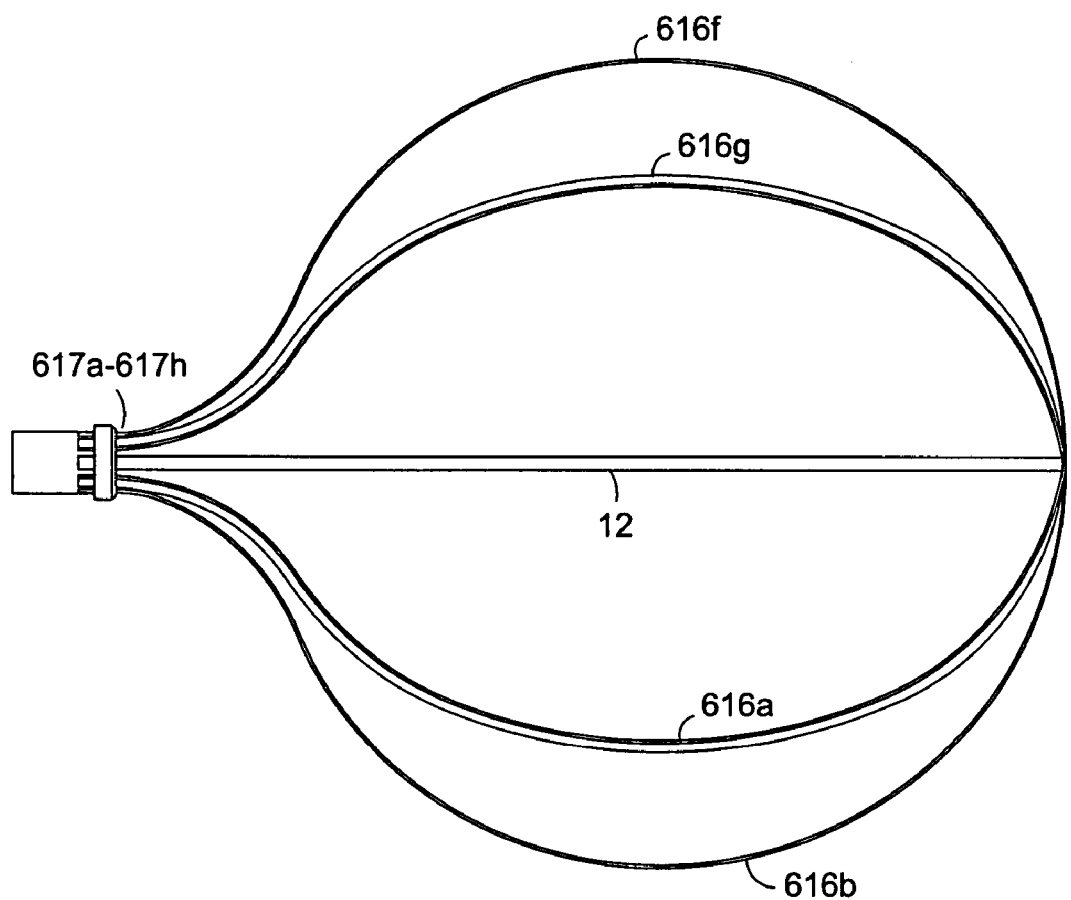
FIG. 17 depicts a side view of the basket assembly of the activation catheter of FIG. 16.
Figure 18:
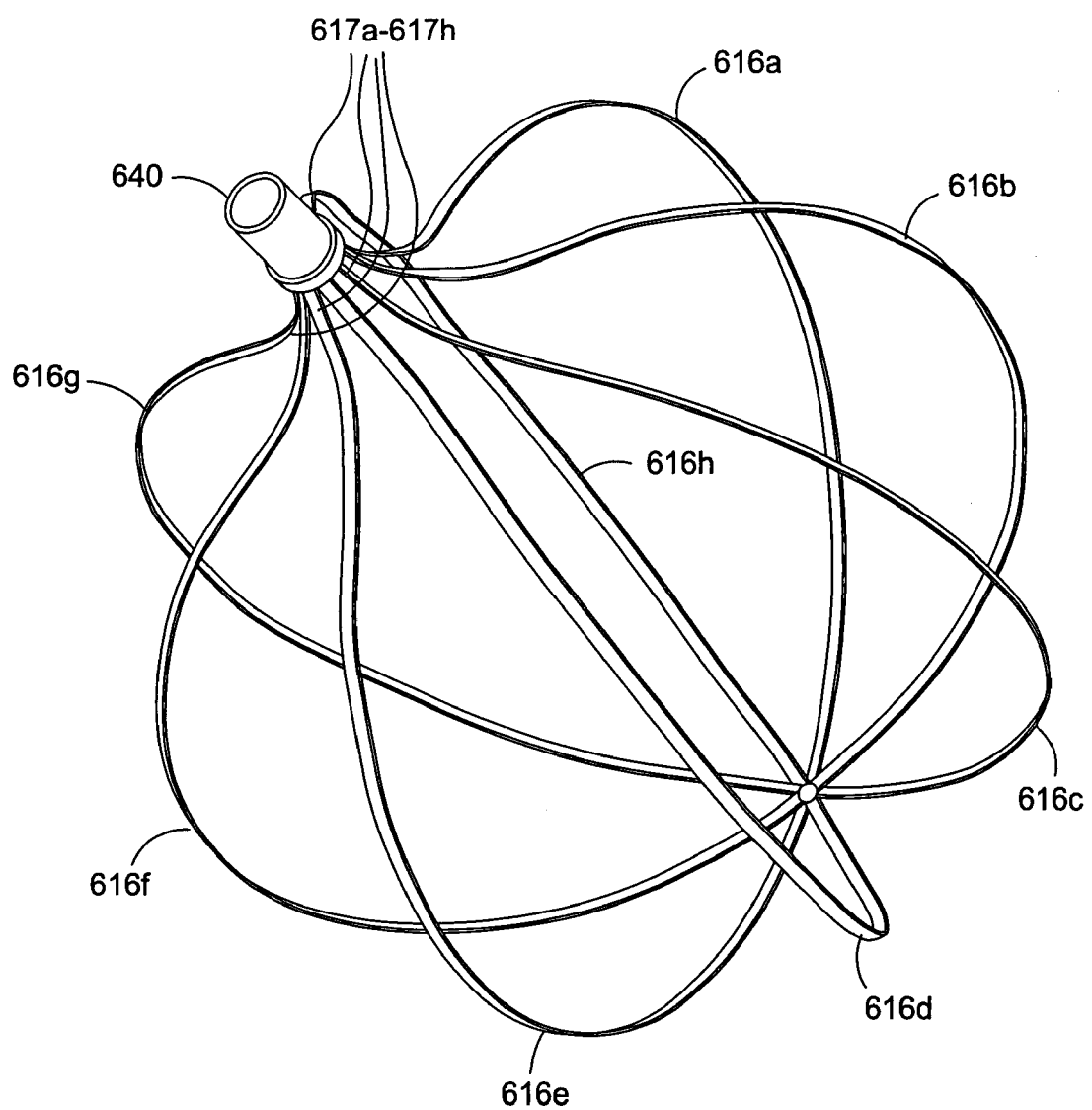
FIG. 18 depicts a back side view of the basket assembly of the activation catheter of FIG. 16.

As shown in FIGS. 16-19, an alternative embodiment of the activation catheter may include a plurality of expandable splines 616a-h forming a basket shaped assembly 630 for effectively engaging the implanted annuloplasty ring. With reference to FIG. 16, the activation catheter has an outer tube 10 including a lumen 11 and an inner tube 12 slidably insertable through the lumen 11 of the outer tube 10. The inner tube may have a guidewire lumen 13 extending along the longitudinal axis and a tip 615 located on the distal end. A plurality of expandable splines 616a-h may be connected at a first connection point 617a-h spaced apart along a circumference of the hollow connection cap 640 located at the distal end of the outer tube and at a second connection point 618a-h spaced apart along a circumference of the distal tip 615 of the inner tub 12. The splines 616a-h may be constructed of a flexible shape-memory material, such as a nitinol wire shape or any other suitable shape-memory material, such that when the inner tube 12 is pulled proximally back through the lumen 11 of the outer tube 10, the splines 616a-h will bow out and expand in diameter forming a basket shaped assembly 630 for engaging the implanted annuloplasty ring. The spline(s) 616a-h may be contracted as much as necessary to provide the basket assembly 630 with the appropriate cross sectional diameter to engage the wall of the patient's left atrium. The wall of the left atrium may then be used as a guide to advance the activation catheter until the basket assembly 630 is abutting the implanted annuloplasty ring 400. Here, the physician may engage the basket assembly 630 with the annuloplasty ring 400 by applying constant force against the expanded splines 616a-h in the direction of the annulus to keep the basket assembly 630 firmly pressed against the annuloplasty ring 400

Figure 19:
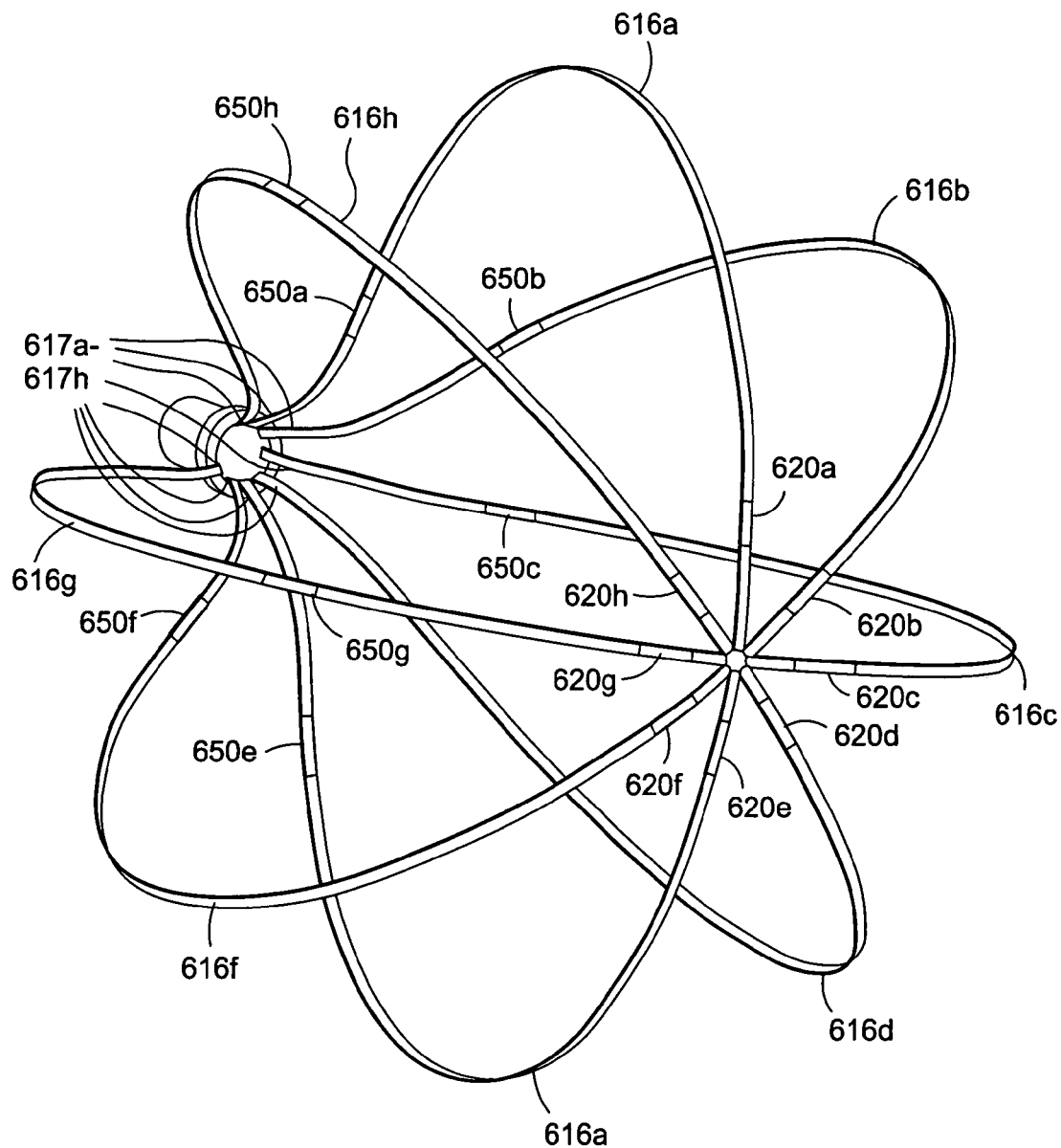
FIG. 19 depicts front side view of the basket assembly of the activation catheter of FIG. 16.

As shown in FIG. 19, in certain embodiments, the splines 616a-h may further include one or more RF heating electrodes 620a-h mounted on the surface of the spline(s). In certain embodiments, the RF heating electrode(s) 20a-b are mounted on the distal end of the splines 616a-h such that when the basket assembly 630 is expanded, the RF electrodes 620a-h are substantially perpendicular to the longitudinal axis of the activation catheter and may thus abut the surface of the implanted annuloplasty ring. However the electrode(s) may be positioned at any location along the surface of the spline that will contact the annuloplasty ring when the spline and ring are engaged. Furthermore, in certain embodiments, each of the RF electrodes 620a-h may be located at different lengths along the longitudinal axis of their respective spline 616a-h such that different points along the width of the implanted annuloplasty ring may be engaged by selectively engaging different RF electrodes 620a-h. In addition, the basket assembly 630 may further include a plurality of markers 650a-h. For example, in certain embodiments, radio opaque markers may be mounted at various lengths along the longitudinal length of the splines 616a-h. In use, the markers 650a-h may be used to determine the location of the basket assembly 630 within the patient's left atrium to effectively position the basket assembly 630 and the RF electrodes 620a-h to engage the implanted annuloplasty ring.

Figure 20:
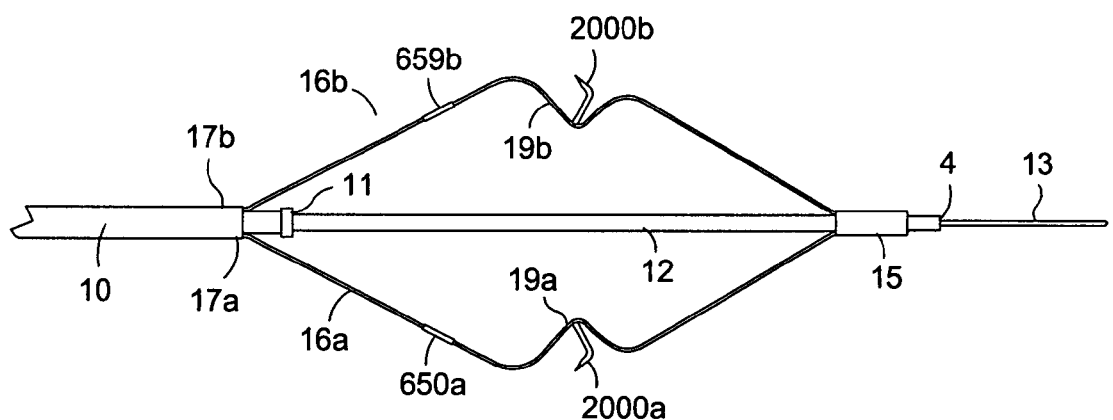
FIG. 20 depicts an alternative embodiment of an activation catheter having needles for engaging an annuloplasty ring.

FIG. 20 depicts an alternative embodiment of an activation catheter having needles 2000a-b for engaging an annuloplasty ring. As shown in FIG. 20, certain embodiments of the activation catheter may include a plurality of needles 2000a-b for effectively engaging the implanted annuloplasty ring. In certain embodiments, the spline(s) 16a-b includes one or more needles 2000a-b mounted on the surface of the spline(s)

16*a-b*. In certain embodiments, the needles 2000*a-b* can be mounted in the dimple(s) 19*a-b*. In certain embodiments, the needles 2000*a-b* may be positioned at any location along the surface of the spline that will contact the annuloplasty ring when the spline and ring are engaged. In certain embodiments, each spline 16*a-b* includes one needle 2000*a-b*. In certain embodiments, each spline 16*a-b* includes a plurality of needles. The needles 2000*a-b* may be conductive strips, plates or wires embedded in or mounted on the spline, a conductive ring encircling a cross section of the spline or any other suitable conductor. In certain embodiments, a needle 2000 comprises a rigid material such as stainless steel, titanium, or the like, or a shape memory material. In certain embodiments, the needles 2000*a-b* can be electrically coupled to a suitable activation energy source, such as an RF generator.

In certain embodiments, once the needles 2000*a-b* are docked against the annuloplasty ring, the needles 2000*a-b* may be activated to deliver activation energy to contact areas on the annuloplasty ring. In certain embodiments, the needles 2000*a-b* may include a thermocouple sensor to measure the temperature at the contact site on the annuloplasty ring while needles 2000*a-b* are transmitting activation energy. The temperature sensor provides real-time feedback to the activation energy generator to regulate the delivery of activation energy to reach and maintain the desired temperature at the annuloplasty ring. For example, in certain embodiments, the activation energy generator compares the temperature information with the user defined set temperature for the contact site on the annuloplasty ring. Once the activation energy generator registers that the contact site is nearing or has reached the preset maximum temperature, the activation energy generator may decrease or completely stop delivering activation energy to the activation energy heating electrode. In certain embodiments, the needles 2000*a-b* may have magnetic properties such that, in use, the needles 2000*a-b* may be attracted to opposite pole magnets located on the implanted annuloplasty ring.

With reference to FIG. 20, the activation catheter has an outer tube 10 including a lumen 11 and an inner tube 12 slidably insertable through the lumen 11 of the outer tube 10. The inner tube may have a guidewire lumen 13 extending along the longitudinal axis and a tip 15 located on the distal end. A plurality of expandable splines 16*a-b* may be connected at a first connection point 17*a-b* spaced apart along a circumference of the hollow connection cap 4 located at the distal end of the outer tube and at a second connection point 18*a-b* spaced apart along a circumference of the distal tip 15 of the inner tub 12. The splines 16*a-b* may be constructed of a flexible shape-memory material, such as a nitinol wire shape or any other suitable shape-memory material, such that when the inner tube 12 is pulled proximally back through the lumen 11 of the outer tube 10, the splines 16*a-b* will bow out and expand in diameter for engaging the implanted annuloplasty ring. The spline(s) 16*a-b* may be contracted as much as necessary to provide the appropriate cross sectional diameter to engage the wall of the patient's left atrium. The wall of the left atrium may then be used as a guide to advance the activation catheter until at least one of the expanded splines 16*a-b* is abutting the implanted annuloplasty ring. Here, the physician may engage the expanded splines 16*a-b* with the annuloplasty ring by applying constant force against the expanded splines 16*a-b* in the direction of the annulus to keep the expanded splines 16*a-b* firmly pressed against the annuloplasty ring.

As shown in FIG. 20, in certain embodiments, the splines 16*a-b* may further include one or more needles 2000*a-b* mounted on the surface of the spline(s). In certain embodiments, the needles 2000*a-b* are mounted on the distal end of the splines 16*a-b* such that when the splines 16*a-b* are expanded, the needles 2000*a-b* are substantially perpendicular to the longitudinal axis of the activation catheter and may thus abut the surface of the implanted annuloplasty ring. However the electrode(s) may be positioned at any location along the surface of the spline that will contact the annuloplasty ring when the spline and ring are engaged. Furthermore, in certain embodiments, each of the needles 2000*a-b* may be located at different lengths along the longitudinal axis of their respective spline 16*a-b* such that different points along the width of the implanted annuloplasty ring may be engaged by selectively engaging different needles 2000*a-b*. In addition, the splines 16*a-b* may further include a plurality of markers 650*a-b*. For example, in certain embodiments, radio opaque markers may be mounted at various lengths along the longitudinal length of the splines 16*a-b*. In use, the markers 650*a-b* may be used to determine the location of at least one of the expanded splines 6*a-b* within the patient's left atrium to effectively position splines 16*a-b* and the needles 2000*a-b* to engage the implanted annuloplasty ring.

Figure 21:
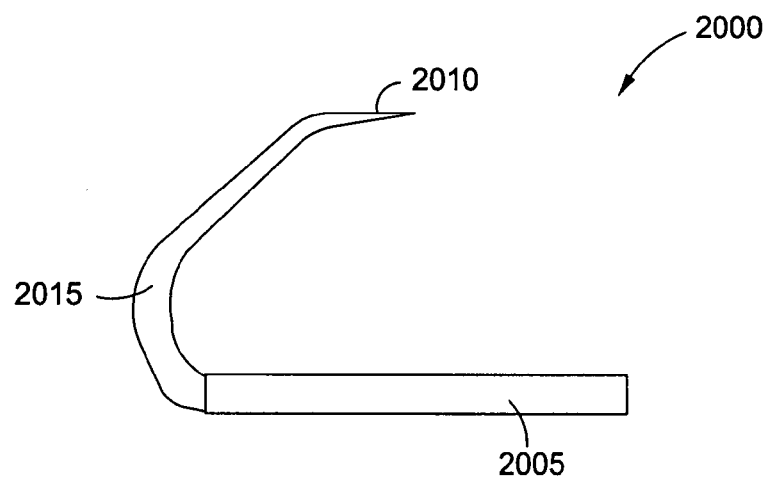
FIG. 21 depicts a side view of an embodiment of the needle of FIG. 20.

FIG. 21 depicts a side view of an embodiment of the needle 2000 of FIG. 20. In certain embodiments, the needle 2000 includes a substantially straight portion 2005 and a substantially curved portion 2015. In certain embodiments, the substantially straight portion 2005 is coupled to the spline 616. In certain embodiments, the substantially curved portion 2015 includes a sharp tip 2010. In certain embodiments, the angle of curve of the substantially curved portion 2015 is about 45 degrees. In certain embodiments, the angle of curve of the substantially curved portion 2015 is about 60 degrees. In certain embodiments, the angle of curve of the substantially curved portion 2015 is about 90 degrees. In certain embodiments, the angle of curve of the substantially curved portion 2015 is about 30 degrees. In certain embodiments, the sharp tip 2010 is angled approximately 15 degrees away from the substantially straight portion 2005 of the needle 2000. In certain embodiments, the sharp tip 2010 is angled approximately 25 degrees away from the substantially straight portion 2005 of the needle 2000. In certain embodiments, the sharp tip 2010 is angled approximately 5 degrees away from the substantially straight portion 2005 of the needle 2000.

In certain embodiments, at least one of the needles 2000*a-b* comprises a sharp end 2010 configured to puncture or otherwise penetrate a thin layer of tissue. In certain embodiments, at least one of the needles 2000*a-b* comprises a sharp end 2010 configured to puncture or otherwise penetrate a surface or layer of an annuloplasty ring. In certain embodiments, after the sharp end 2010 of a needle punctures a thin layer of tissue and/or a layer of an annuloplasty ring, such as a Dacron® or silicon-rubber layer, as described above, the needle may engage a contact area of the annuloplasty ring and thereby deliver activation energy to a region of the annuloplasty ring.

In certain embodiments, the needles 2000*a-b* may be used as an anchoring mechanism so as to facilitate the catheter remaining in substantially the same place during an activation of the annuloplasty ring. For example, in certain embodiments, the needles 2000*a-b* may penetrate and anchor in nearby tissue. In certain embodiments, the needles 2000*a-b* may penetrate and anchor in portions of the adjustable annuloplasty ring.

While certain embodiments of the invention and variations thereof have been described in detail, other modifications and methods of using and medical applications for the same will be apparent to those of skill in the art. Accordingly, it should be understood that various applications, modifications, combinations, sub-combinations and substitutions may be made of equivalents without departing from the spirit of the invention or the scope of the claims.

What is claimed is:

1. An activation device, for applying energy to an implanted annuloplasty ring, comprising:
   an outer elongate member having an outer elongate member distal end and an outer elongate member proximal end, and a lumen therebetween;
   an inner elongate member having an inner elongate member distal end and an inner elongate member proximal end, wherein the inner elongate member is disposed within the lumen of the outer elongate member;
   at least one elongate flexible element having an elongate flexible element proximal end and an elongate flexible element distal end, the elongate flexible element distal end connected to the inner elongate member distal end and the elongate flexible element proximal end connected to the outer elongate member distal end, wherein the elongate flexible element is configured to advance radially outward as the inner elongate member distal end is drawn proximally toward the outer elongate member distal end;
   and at least one energy-transfer element disposed within a medially-disposed concavity of said at least one elongate flexible element, said medially-disposed concavity configured to receive the annuloplasty ring, wherein said at least one energy-transfer element comprises a radially outwardly extending penetrating member, said penetrating member configured to penetrate an outer surface of the annuloplasty ring.

2. The activation device of claim 1, wherein the at least one energy-transfer element comprises an electrode.

3. The activation device of claim 2, wherein the electrode comprises an RF electrode.

4. The activation device of claim 1, wherein the at least one energy-transfer element comprises a needle.

5. The activation device of claim 4, wherein the needle comprises a substantially straight portion and a substantially curved portion.

6. The activation device of claim 1, wherein the inner elongate member further comprises a distal tip positioned at the inner elongate member distal end and wherein the elongate flexible element distal end is coupled to the distal tip.

7. The activation device of claim 1, wherein the elongate flexible element comprises a shape-memory material.

8. The activation device of claim 1, comprising a plurality of elongate flexible elements.

9. The activation device of claim 1, further comprising a handle connected to said outer elongate member, said handle configured to permit a user to lock said inner elongate member in place with respect to said outer elongate member.

10. The activation device of claim 9, wherein the proximal end of said inner elongate member extends through a lumen of said handle, said handle comprising a slidable knob extending through a longitudinal opening in a body portion of said handle, said knob configured to engage said inner elongate member.

11. The activation device of claim 1, further comprising a cooling system configured to deliver cooled liquid to tissue surrounding said annuloplasty ring.

* * * * *